United States Patent [19]

Kline

[11] 4,243,687
[45] * Jan. 6, 1981

[54] FREEZE-DRIED NATURAL SOUR DOUGH STARTER

[76] Inventor: Leo Kline, 1828 Mendocino St., Richmond, Calif. 94804

[*] Notice: The portion of the term of this patent subsequent to Feb. 20, 1996, has been disclaimed.

[21] Appl. No.: 2,476

[22] Filed: Jan. 10, 1979

Related U.S. Application Data

[62] Division of Ser. No. 805,681, Jun. 13, 1977, Pat. No. 4,140,800.

[51] Int. Cl.³ .............................................. A21D 8/04
[52] U.S. Cl. ..................................................... 426/62
[58] Field of Search ....................... 426/18, 19, 20, 61, 426/62, 654

[56] References Cited

U.S. PATENT DOCUMENTS

| | | | |
|---|---|---|---|
| 3,734,743 | 5/1973 | Kline et al. | 426/18 |
| 3,891,773 | 6/1975 | Kline et al. | 426/61 |
| 3,897,307 | 6/1975 | Kline et al. | 426/61 |
| 3,897,307 | 7/1975 | Porubcan et al. | 426/61 |
| 4,053,642 | 10/1977 | Hup | 426/61 |

*Primary Examiner*—Raymond N. Jones
*Assistant Examiner*—Elizabeth A. Hatcher
*Attorney, Agent, or Firm*—Townsend and Townsend

[57] ABSTRACT

A freeze-dried sour dough French bread starter culture, or baking additive for other purposes, is prepared by inoculating an unsterilized and unpasteurized flour-water-salt suspension with a natural mother or starter sponge containing numerous naturally occurring and closely related strains of *Lactobacillus sanfrancisco*, and also containing substantial levels of the natural fermentations acids, lactic and acetic; incubating said mixture at about 82° F. until a specified acidity level is reached corresponding to about $2 \times 10^9$ viable bacteria per gram; cooling to about 55° F., and adding stabilizers compatible with the flour system, in particular certain disaccharides; freezing under moderate conditions ($-10°$ to $-25°$ F.) without first separating the cells from the flour medium; followed by conventional freeze-drying in vacuo (vacuum of approximately 50 to 200 microns) to a moisture content in the final product of about 2%.

16 Claims, 1 Drawing Figure

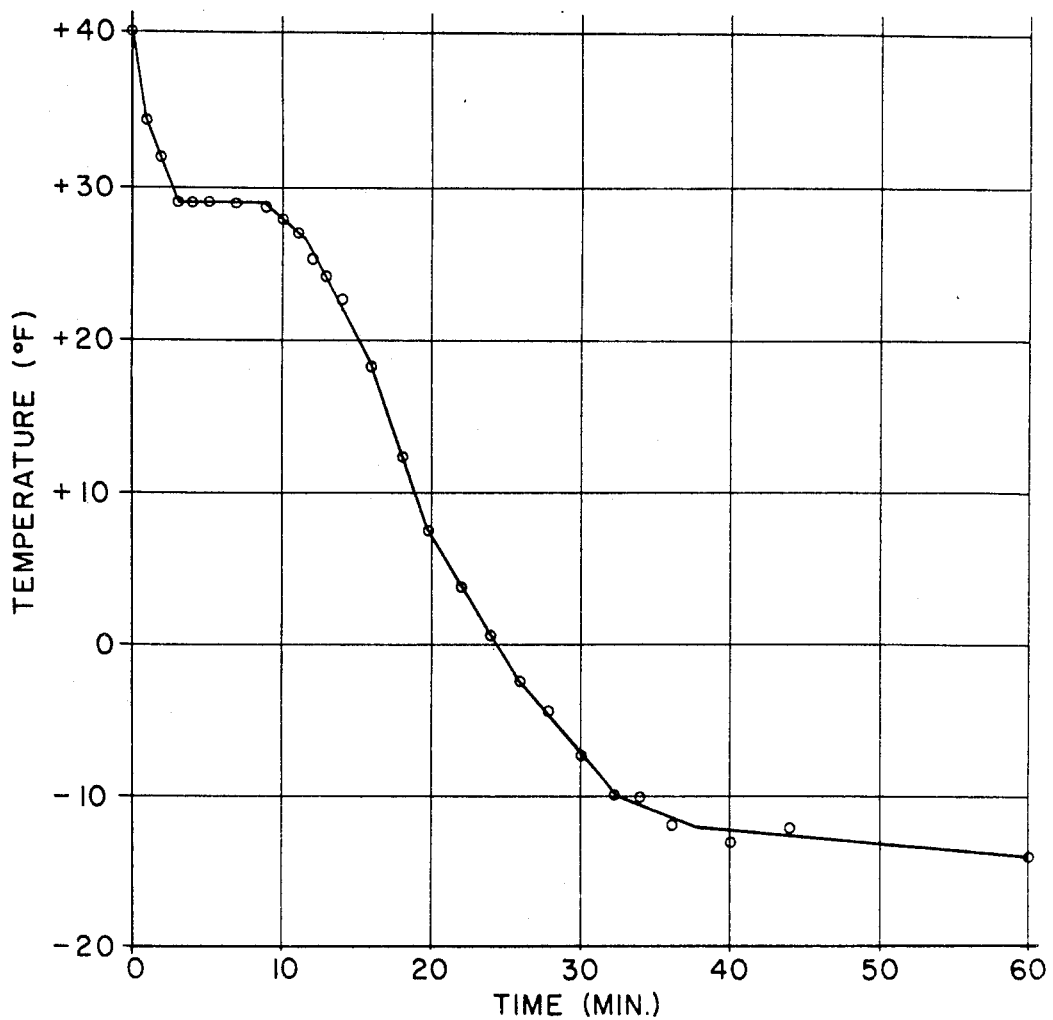
FIG.—1.

FREEZE-DRIED NATURAL SOUR DOUGH STARTER

This is a division of application Ser. No. 805,681, filed June 13, 1977 now U.S. Pat. No. 4,140,800.

FIELD OF THE INVENTION

This invention relates to a freeze-dried sour dough bakery product and a method for its preparation. The freeze-dried product is principally designed as a starter for French bread and is also suitable for other bakery applications as a flavoring additive, as a source of acids, and for inclusion in other bakery products such an English muffins.

BACKGROUND OF THE INVENTION

Sour dough French bread is a special kind of bread having unique properties including its particular crustiness and sour taste. In the U.S. the true article is manufactured virtually only in the San Francisco Bay area. There the product has been produced continuously for over 100 years and commands a market estimated to be 15–20% of all bread consumed.

The bread made in the San Francisco area employs a process primarily dependent on the use of a starter or mother sponge which is in the form of a piece of heavy dough. The present invention employs this natural starter. The term natural refers to this form of starter which has been perpetuated in practical bakery use for over 100 years without going through the steps of extracting the active agents therefrom, growing them out in artificial media and then separating out the active agents and concentrating and stabilizing them for further use.

The present invention is designed to provide an improved starter which can be readily distributed to all other parts of the world so that the true sour dough French bread now available in San Francisco can be made available in these places.

BRIEF DESCRIPTION OF THE PRIOR ART

Kline U.S. Pat. Nos. 3,734,743 and 3,891,773 relate to the manufacture of sour dough French bread in connection with a pure culture of Lactobacillus sanfrancisco. Olson U.S. Pat. Nos. 3,404,984 and 3,547,654 relate to the growth of different bacteria on pasteurized synthetic growth medium as a product used to enhance bread flour. Freeze-drying is not involved. Kirby U.S. Pat. No. 2,322,940 teaches the inoculation of sterilized broth medium with pure cultures of an unrelated bacteria. After incubation, cells are separated and admixed with flour and/or shortening. No stabilizers are added and freeze-drying is not involved. German Pat. No. 933,441 teaches the use of a pure culture of different bacteria on rye meal to inoculate a growth media in which the flour media comprises only 10% rye meal. The desired end product is not a sour dough French bread. British Pat. No. 980,384 involves a different bacteria culture at a different temperature which is used primarily for leavening. The growth medium contains only about 1% of flour. Sing U.S. Pat. No. 4,021,581 describes a process for freezing Lactobacillus sanfrancisco without first separating the cells, while Porubcan U.S. Pat. No. 3,897,307 describes a freeze-drying process for other types of bacteria in which cells are not first separated.

SUMMARY OF THE INVENTION

In accordance with the present invention a freeze-dried bakery composition is provided which comprises Lactobacillus sanfrancisco (*L. sanfrancisco*) in a flour culture media which has been subjected to incubation conditions suitable for the growth of said bacteria prior to freeze-drying, the gluten of said flour being substantially undeveloped during said incubation, and a frozen residue of water. The product may be prepared by the process of this invention which comprises inoculating a nonsterile flour-water-salt suspension with a natural sponge containing *L. sanfrancisco,* incubating said inoculated suspension under conditions which produce an effective concentration of viable bacteria, cooling said growth suspension, adding at least one stabilizer for the cultured bacteria, freezing said stabilized suspension and drying the frozen product.

The resulting novel preparation lends itself to industrial scale production as compared to existing commercial frozen or freeze-dried starters of *L. sanfrancisco* which utilize pure culture-aseptic techniques and are flash frozen on a very small scale in liquid nitrogen (about $-300°$ F.) or dry ice-solvent mixtures (about $-110°$ F.).

Moreover, the products of this invention can be distributed and held for several months under moderate and readily available above-freezing temperature conditions ($+35°$ F. to $+55°$ F.) without important loss of activity, in contrast to existing frozen preparations which must be distributed in dry ice or liquid nitrogen and held by the user in special freezing equipment at $-40°$ F. or below. Since the product of this invention is a free-flowing powder it can be more conveniently and safely used by the baker without the need for technical expertise to avoid thawing damage.

Of particular significance is the finding that this new product is markedly and unexpectedly superior in activity to existing frozen or freeze-dried preparations of *L. sanfrancisco.* Thus, when introduced into a flour system in the first stage of the baking application, numbers of viable and fully active cells of *L. sanfrancisco* are found to increase 10 to 25-fold before growth even commences with existing commercial preparations of *L. sanfrancisco.* This shorter "lag" period and much lower cost of production permit elimination of at least one step in its application to bread or other baked products as compared to existing commercial frozen or freeze-dried preparations.

Finally, this product contains sufficient naturally produced levels and proportions of lactic and acetic acids that, under some conditions of usage in baking, no supplementation with artificial or synthetic acids is necessary as is always the case with existing commercial preparations.

DESCRIPTION OF THE PREFERRED EMBODIMENT

Although, as will be shown, there is some latitude in the conditions for making the present product, a preferred embodiment is illustrated at this point to provide insight into the nature of the process before the limits of specific conditions are described:

Prepare slurry of following porportions:

| Actual | Basic Proportions |
| --- | --- |
| 150 g. mother sponge | 20 |

| Actual | Basic Proportions |
|---|---|
| 750 g. Hi gluten flour* | 100 |
| 1875 g. water | 250 |
| 17 g. salt | 2.2 |

*14.7% protein

These particular amounts and proportions lend themselves to being blended at reduced speed in a 5 quart Waring blender and being transferred to three 2-liter Erlenmeyer flasks for mild agitation during subsequent incubation at 80°–82° F. After 8 hours development the pH had decreased from 5.50 to 3.84; the flasks were then transferred and held in a 55° F. storage incubator for an additional 2½ hours during which time the pH dropped further to 3.74. At this point a stabilizer solution, also at 55° F., containing 220 g. of sweet whey solids in 660 g. of water was blended with the slurry in the Waring blender. The 220 g. of sweet whey solids represented 6% by weight of the final slurry containing the stabilizer. 2000 ml. of the final slurry at about 55° F. was poured into a stainless steel tray approximately 35"×12" which had been pre-chilled in a blast freezer operating at −15° to −20° F. This resulted in a layer between ¼" and ⅜" deep. Air flow in the blast freezer was 500 linear ft./min. After about 45 minutes in the blast freezer, with the product at −15° F., the tray was transferred to a freeze dryer and dried 18 hours at a vacuum of 50 to 100 microns with the shelves "warmed" to 70° F. for the last 10 hours. Product was readily removed from the tray and optionally passed through a Fitzmill operated at low speed and using a screen containing holes 0.0635" in diameter to yield a free-flowing non-dusty powder. There was virtually no residence time in the mill, no temperature increase in the product (1° F. for less) and no loss in viable count due to milling in this manner.

Some data from this run are as follows:

A. Slurry

|  | pH | Viable count/ml. L. sanfrancisco | Viable count/ml. T. holmii |
|---|---|---|---|
| Initial | 5.50 | $8.0 \times 10^7$ | $7.6 \times 10^5$ |
| + 8 hr. 80° F. | 3.84 |  |  |
| + 2½ hr. 55° F. | 3.74 | $1.7 \times 10^9$ | $2.9 \times 10^7$ |
| + 6% sweet whey solids | 4.28 |  |  |

B. Freeze-Dried Powder contained:
2.0% water
22.4% stabilizer solids (sweet whey)
$2.1 \times 10^9$ L. sanfrancisco/g (stab.-free) = 35% recovery
less than $1 \times 10^4$ T. holmii/g. (stab.-free) = <0.01% recovery

C. Activity of Freeze-dried powder

| Assay mixture: | 9.02 | g. powder (=7.0 g. stab.-free basis) |
|---|---|---|
|  | 50 | g. Hi gluten flour |
|  | 125 | ml. water |
|  | 1.1 | g. salt |

Incubate 80–82° F. with mild agitation

| Time (Hours) | pH | pH drop | L. sanfrancisco | Multiplication |
|---|---|---|---|---|
| 0 | 5.24 | — | $6.9 \times 10^7$ | — |
| 3½ | 4.72 | 0.52 | $4.6 \times 10^8$ | 7 |
| 5½ | 4.08 | 1.16 | $1.6 \times 10^9$ | 24 |
| 7 | 3.78 | 1.46 | $2.1 \times 10^9$ | 32 |

*counts from similar sample used

D. Comments

The above sample run illustrates: (a) the effectiveness of the flour medium and natural inoculum in promoting growth of L. sanfrancisco; (b) the excellent recovery of viable bacteria achieved with the aid of the selected stabilizer used and without the need for flash freezing or separating the cells from the flour growth medium; (c) the superior activity of the final starter culture preparation in terms of short lag period or rate of multiplication. Also shown clearly is the failure of the sour dough yeast, T. holmii, to survive the freeze-drying process.

PARAMETERS OF THE INVENTION

1. Inoculum or Seed

(a) Mother Sponge

Conventional mother sponge, as routinely available on a daily basis in commercial San Francisco sour dough French bread bakeries, is used as the preferred seed or inoculum of L. sanfrancisco. It contains a high count (1 to $3 \times 10^9$ per g.) of closely related, but not identical, naturally occurring strains of L. sanfrancisco and is prepared in ordinary bakery equipment from flour and water without special sanitary precautions. This is in contrast to existing commercial preparations which utilize costly pure culture techniques generally involving selection of a single strain cultivated on agar slants or stabs which is eventually, by a step-wise procedure, cultivated in a pasteurized or sterilized broth.

The mother sponge also contains lesser numbers of the sour dough yeast (about 1.5 to $3 \times 10^7$ per g.), T. holmii, whose presence is advantageous in the preferred embodiment of this invention. T. holmii contributes to the selective growth of L. sanfrancisco both in the mother sponge and in the flour slurry cultures of this invention prepared from mother sponge. T. holmii does not utilize maltose, a sugar required by L. sanfrancisco for rapid and heavy growth, and thus not only does not interfere with the growth of the latter but may actually enhance it. Experience has shown that the combination of these two microorganisms in a flour system virtually precludes growth of contaminating bacteria, making sanitary precautions such as pasteurization or sterilization unnecessary. As shown above in the example of the preferred procedure, the viability of the T. holmii cells is destroyed by freeze-drying, so that this yeast is not, however, part of the final product of this invention.

The use of mother sponge as the inoculum or seed of L. sanfrancisco in this invention has the following advantages:

(1) Available in industrial quantities (hundreds of pounds) at very low cost;

(2) Highly reliable—has been perpetuated by lay (nontechnical) bakery personnel for decades without trouble;

(3) Has high counts of fully active cells of L. sanfrancisco, which counts are as high or higher than those developed with pure culture seeds grown on synthetic (non-flour) sterilized or pasteurized broths;

(4) Contains multiple strains allowing for natural selection of superior strains during freeze-drying (different strains are evident from colony differentiation in plating procedures and in the varying nutritional requirements and rates of growths of different strains isolated from the same mother sponge).

(5) In addition to being a source of *L. sanfrancisco* for seed purposes, the mother sponge also contributes unique growth-promoting substances which are carried over into the final product and naturally produced lactic and acetic acids which, under recommended conditions, automatically provide for optimal initial pH adjustment (pH 5.4±0.2) of the flour slurry medium.

In practice, the freshly prepared (rebuilt) mother sponge is allowed to develop at 76°–83° F. preferred) until a pH of 3.9–4.1 (preferably 3.95–4.05) is reached. At this point the bacteria are largely in the late logarithmic stage of growth desirable for seed purposes. The nearly, but not quite fully developed mother sponge may, however, be held for an additional 4–6 hours at 55° F. without important impairment of its seed value. The use of higher incubation temperatures as, e.g., 86°–91° F., which promote more rapid growth of *L. sanfrancisco*, are not recommended as the bacteria pass through the late logarithmic phase too rapidly for the system to be reliable.

One may wonder why the obvious and simple procedure of just diluting a fully developed and readily available (in the sour dough bakery) mother sponge with water, to a consistency desirable for freeze-drying, is not resorted to instead of going through the process of this invention. However, as shown in Example 1, the use of diluted mother sponge is unexpectedly and decidedly unsuccessful. The freeze-dried product obtained from it is only 1/10th to 1/40th as active as the comparable samples prepared by the process of this invention. Apparently the fully developed gluten in a mother sponge interferes with, or does not contribute to, the protective powers of the flour system and stabilizer in the freeze-drying process. Gluten in the liquid flour slurry cultures is not developed nor is it subjected to development prior to the freeze-drying step.

(b) Liquid Mother Sponges

These are variations of the conventional mother sponge and they contain a much higher proportion of water. Thus, mother sponge is, of course, a stiff heavy dough containing flour:water in the proportions of approximately 1:0.45 while liquid sponges such as those used as growth media in the process of this invention contain flour:water in the proportions of 1:1 to 1:2.5. A small amount of salt (about 0.9% of the water phase) is also included in the liquid sponges and has some benefits to be discussed later. The liquid sponges are first prepared by using mother sponge as an inoculum but then may be perpetuated by transferring directly from liquid sponge to liquid sponge. If this is done with approximately 5–15% by weight of the total flour in the new liquid sponge being derived from the previous fully developed liquid sponge (10–12% preferred), then the necessary initial acidification to pH 5.4±0.2 is automatically obtained and sufficient massive inoculation of *L. sanfrancisco* and *T. holmii* is made to assure adequate protection against contaminants developing.

Liquid sponges as seeds are, however, not quite as safe in the hands of non-technical personnel and require special additional tankage and other equipment as well as special preparation.

(c) Use of Freeze-Dried Product of This Invention as Seed

The product of this invention may also be used as seed and, as illustrated in Example 2, is, surprisingly, virtually as good as mother sponge, suggesting that many of the advantages of the latter are carried over. A two-step process as illustrated in Example 2 is desirable, but not necessary, to fully activate the *L. sanfrancisco* cells and to reduce the cost of the seed. Also, of course, the freeze-dried product of this invention used as seed does not contain *T. holmii* and thus reduces the safety factor inherent with the use of mother sponge per se.

In Example 2 it is noted that, in preparing the second and final liquid slurry culture, a smaller seed in terms of flour transferred was used in A (preferred method freeze-dried=5.8%) than with the slurry prepared from the usual mother sponge seed, B (12%). This was done to achieve approximately the same level of inoculum of *L. sanfrancisco* cells since the preferred method freeze-dried product had roughly twice the density of cells per unit weight of flour as that derived from the mother sponge.

Example 2 also illustrates the use of 7.5% maltose, a preferred stabilizer, in improving recovery of viable cells of *L. sanfrancisco* approximately 40–50 fold.

(d) Laboratory Pure Cultures

Laboratory cultures of *L. sanfrancisco* carried on pure culture agar slants or stabs and grown out in synthetic broth media can, after several transfers to activate the cells, also be used to inoculate the flour slurry media of this invention. However, this is counterproductive from the standpoint of this invention in requiring multi-step pure culture techniques and in limiting the number of pure culture strains which must arbitrarily be selected. Moreover, the final product prepared in this manner has not, to date, been found to be as active.

(e) Commercial Pure Cultures (starter culture preparations)

The use of commercial freeze-dried or frozen cultures as seed for the flour slurry media of this invention may also be used but have two distinct disadvantages: (1) high cost, and (2) substantially lower activity of the cells in the final freeze-dried product apparently due to weakening or injury to the cells caused by commercial processing in non-flour media. This latter point is illustrated in Example 3. (Not shown are the preparation of the liquid slurries which were similar to those used for the preferred method freeze-dried product in Example 2 excepting that artificial acidification must be used with the commercial cultures for initial pH adjustment and, also, the extreme sluggishness of the commercial culture requires a longer incubation period in the first step.) It is clear from Example 3 that, while use of commercial cultures as seed may give comparable counts in the final freeze-dried product, the activity of the cells obtained are markedly inferior.

2. Flour Media and Incubation Conditions (a) Flour Concentration

The natural flour substrates for *L. sanfrancisco*, namely mother sponge and bread dough, do not lend themselves to freeze-drying directly since their viscous nature makes sufficiently rapid freezing impractical and slow freezing is highly detrimental to the survival of the bacteria in any system. Even if they could be frozen and dried efficiently, they also have the disadvantage of drying to a rock-hard consistency requiring strenuous milling to powder the product, and such milling generates heat in the product and additional damage. As has already been shown (Example 1) the alternative of diluting mother sponge with water to a consistency desirable for freeze-drying also does not work.

On the other hand, in preparing more dilute flour slurry media for inoculation and growth, one has to also consider that if the flour is diluted excessively for the purpose of improving the freeze-drying characteristics, then the nutrients necessary for growth may be diluted to the point that rate and degree of growth are greatly reduced. Thus, part of the essence of this invention is selection of an optimal range of flour:water ratios which combine excellent growth and freeze-drying characteristics. Example 4 illustrates these effects in a preliminary way with a flour:water ratio of 1:2.5 giving the best results of those ratios tested.

The most concentrated system that did give a measure of success was one prepared with a flour:water ratio of 1:1 as shown in Example 5 (C). Such a mixture is, in fact, a very viscous paste which does not require any agitation to prevent settling but is thin enough to be pumpable. Although highly effective as a growth medium, this 1:1 flour culture must be diluted for successful freeze-drying. Thus, as shown in Example 5, freeze-drying without dilution (cf. samples without stabilizer added) results in markedly reduced counts and activity of *L. sanfrancisco* and also was found to yield a quite hard product which was pulverized only with difficulty. On the other hand, if diluted from 1:1 to 1:2.5 after culturing and just before freeze-drying, and stabilizer added, a product is obtained which is comparable in count and activity to that obtained with the 1:2.5 slurry used directly as a culture (Example 5 (B)).

Example 5 also illustrates the general, and highly important finding, that yield of *L. sanfrancisco* cells obtained with a slurry culture is roughly twice that obtained in a mother sponge when compared on a flour or on a dry basis. This finding was unexpected and of importance in the success of the process of this invention.

Example 6 illustrates the comparison of flour:water cultures in ratios of 1:1.5 and 1:2.5. The 1:1.5 suspension is approximately the most viscous that can be prepared which not only requires little or no agitation during development but, also, can be freeze-dried directly without further dilution. In the study shown, the product prepared from it was comparable or slightly superior to that prepared from the more commonly used 1:2.5 suspension. The 1:1.5 suspension is slightly thick for optimal freeze-drying but the addition of stabilizer as a water solution containing 20–35% solids reduces its viscosity to the point where freeze-drying characteristics are excellent and the product is highly friable and pulverizes with great ease.

Before summarizing the results on flour concentration, it should be mentioned that the most commonly used 1:2.5 suspension does require mild agitation to keep the flour suspended and to insure uniformity in the final product.

Thus, in summary, flour:water cultures in the proportions of 1:1 to 1:2.5 will generally be used (1:1.5 to 1:2.5 preferred) with the choice depending upon the type of equipment available for preparing the slurry or paste, for keeping it agitated if necessary during development and holding, and for implementing the necessary temperature control during development, cooling and holding, and addition of stabilizer. More dilute flour concentrations could be used in conjunction with other appropriate nutrients. Economics must also be considered—obviously the most concentrated slurry that lends itself to maximum quality of freeze-dried product would be preferred from the standpoint of minimizing freeze-drying costs—providing all other factors involved in handling fall into place.

(b) Type of Flour

A first consideration is, of course, that the flour used is one suitable for bread manufacture, i.e., is one in which the amylase content and free starch content of the flour are assured by amylograph or other quality control measure. These two factors are essential in the formation of maltose (to a level of over 5% by weight of the flour) after water is mixed with the flour. Maltose is required by *L. sanfrancisco* for rapid and heavy growth.

While maltose formation is not related to the protein content, high gluten (high protein) flours are used in the preferred process of this invention as they were found to give more reliable and consistently better results as illustrated in Example 7. However excellent results have occasionally been obtained from lower protein flours so it is recognized that flours standardized for bread manufacture and containing between about 11 and 15% protein may be used with more care and skill necessary in culturing with the lower protein flours. Wheat gluten may also be used as an adjunct to increase protein content but generally this would not be desirable from a cost standpoint.

(c) Level of Inoculum (seed)

In the case of the flour slurry culture of this invention the safety and reproducibility of the process require a relatively high level of inoculation as well as initial acidification to assure minimization of competition from contaminants since the flour system does not lend itself to pasteurization or sterilization. A preferred inoculum would provide an initial count of about $5 \times 10^7$ or $2 \times 10^8$ per ml. and an acidification with lactic and acetic acids in their normal proportions to give an initial pH of about 5.3–5.6. Experience has shown that both of these are accomplished simultaneously with any flour-based inoculum (as e.g., mother sponge, liquid sponge or slurry, or the present freeze-dried product) if the initial flour slurry culture (flour:water = 1:2.5) is made up with about 10–12% of the flour being contributed by the flour from the inoculum (cf. A Step 1 and B Step 2 in Example 2). Subsequently, in transferring from liquid slurry to liquid slurry which have higher acid and bacterial densities, only about 6% of the flour need come from the previous stage (cf. A Step 2 in Example 2). These levels of inoculation or transfer in terms of the percentage of flour being transferred from the previous stage have been found to be very reliable guidelines for accomplishing the necessary pH adjustment.

In terms of weight percentages of inoculum for the preparation of liquid slurries, approximate figures would be 5.4% of mother sponge or liquid sponge seeds or 3.8% of the preferred embodiment freeze-dried product seed. These levels of inoculation give the desired initial counts in the range of $5 \times 10^7$ to $2 \times 10^8$ per gram.

While it is not considered reliable in the hands of lay personnel to use lower levels of inoculation in the range of $5 \times 10^6$ to $2 \times 10^7$ per gram, these levels may be used in the hands of skilled personnel along with supplementation with lactic and acetic acids and longer periods of incubation (12 to 14 hours). However, it is desirable in these cases to pretest the flour for absence of competitive contaminants and to be sure the inocula used are fully active (i.e., have short lag periods of growth).

(d) Temperature-Time Conditions for Developing and Holding

As mentioned earlier, although 86° F. is considered the optimal temperature for growth of *L. sanfrancisco*, a growth temperature of about 80° F. (77°-83° F.) is preferred as it permits more stability of culture in the final stages of development for holding and freeze-drying. However, even at 80° F. excessive holding for even a few hours at the high acidity level of the final stages of culture (pH about 3.7) can be harmful to the recovery of numbers of viable bacteria in the freeze-drying process and even more detrimental to their activity even if viable. This is illustrated in Example 8 where an additional $4\frac{1}{2}$ hours of holding at 80° F. was significantly detrimental to the activity of the cells in the final freeze-dried product and holding 9 hours at 80° F. was devastating both to activity and viable count. On the other hand, it has been found not only not damaging but advantageous to cool the flour culture at a propitious time (pH 3.70-3.85, depending on how long it is to be held) to 50°-60° F. (55° F. preferred) where growth continues at a reduced rate. This can be accomplished by transferring to refrigerated holding rooms, use of jacketed tanks or other equivalent means. As shown in Example 8, the flour culture transferred to 55° F. at pH 3.74 showed continued growth and activity improvement for up to 9 hours and probably for even longer (12 to 16 hours). Even longer holding periods for up to at least 24 hours at 55° F. are feasible if the flour culture is transferred to this temperature at a higher pH, i.e., about 3.80-3.85.

Thus, cooling the flour culture, preferably to about 55° F., at a selected point of development (pH of 3.70-3.85 in a 1:2.5 flour:water slurry) is an integral part of this process for stabilization of cells prior to freeze drying. It is further advantageous in providing for the safe addition of stabilizer solids or solutions without harmful temperature increase and to achieving a prechilling condition prior to freeze-drying to accelerate the rate of freezing.

(e) Neutralization or pH Adjustment During or After Culturing

It is common practice in commercial culturing of lactic acid bacteria to add KOH, NH$_4$OH or other alkali, during growth to maintain the pH of the culture in the region of pH 5.5-7.0. This is done to promote heavier growth by "neutralizing" the otherwise harmful effects of the metabolic acids produced. However, as shown in Example 9, "neutralization" with 4 N KOH either during or after growth appears unnecessary and even undesirable from the standpoint of recovery of cells and their activity in the final freeze-dried product. Additionally, in the present case, where pasteurization or sterilization of the flour medium is not feasible, the production of metabolic acids, in particular acetic, which are tolerated better by *L. sanfrancisco* than by most contaminants, is considered an advantage or safety feature of the process. "Neutralization", converting undissociated acid into the salt form which is much less toxic to bacteria, would thus be counterproductive in the present case.

The comparison with addition of NFMS as a stabilizer in Example 9 is included to show that the limited beneficial effects of this stabilizer are not attributable to its neutralizing effect.

(f) Use of Salt in the Flour Media

Salt is not used in the conventional mother sponge formulae as those commonly used in San Francisco bakeries, as its low water content and its relatively high acidity range of development (initial pH about 4.8 and final about 3.8-3.9) would not tolerate addition of significant levels. However, it was found that addition of salt at levels between 0.8 and 3.0% of the water phase to be beneficial in the flour slurry cultures of this invention. These levels of salt have only a slight beneficial effect on the rate of growth of *L. sanfrancisco* but a marked effect on increasing the rate of growth of the sour dough yeast, *T. holmii*, and thereby contributing to the safety of the process. Additionally, experience has shown that the use of salt combined with initial acidification and use of a large inoculum of *L. sanfrancisco* all contribute to the safety and reproducibility of the process. Generally, levels of 0.8-0.9% salt, as percent of the water phase, were used in the final flour slurry media developed for freeze-drying. Higher levels up to 3.0% while not harmful for growth were considered less desirable for freeze-drying due to the concentration effect of the process.

(g) Miscellaneous

It is customary in commercial preparation of bacterial starter cultures (exceptions are noted in the "PRIOR ART" section) to separate the cells from the growth media and even wash them before stabilizing for freezing or freeze-drying, as the metabolic products of growth are considered harmful to these bacteria in further processing. The situation is unexpectedly different in the present case where factors in the flour media were found to be beneficial rather than harmful to *L. sanfrancisco*. Accordingly, a unique feature of this invention is the practice of not removing the *L. sanfrancisco* cells from their flour slurry media and adding any stabilizer used directly thereto.

As mentioned in (f) above, neutralization during growth is not advantageous in the process of this invention. From this is derived the distinct advantage that pH measurement can be used as an indicator of the critical end point of culturing where cooling is to be initiated. Where neutralization is employed, other devices not as sensitive, such as optical density or total amount of alkali added or just time of culturing, must be relied on.

It is apparent that the range of flour slurries feasible under the process of this invention might require varying equipment for preparation, holding, cooling, etc. Since such equipment is commonplace in the bread industry for dough and slurry preparation, as well as heating and cooling of the latter, there is nothing unique in the selection of such equipment and such selection is, thus, not a part of the invention.

3. Stabilizers for Minimizing Freeze-Drying Damage

(a) Non-Fat Milk Solids, Monosodium Glutamate and Tween 80

The first stabilizer examined in some detail was non-fat milk solids (NFMS) since this is probably the most commonly used in freeze-drying lactic acid bacteria cultures. Benefits obtained with NFMS were significant but not large as shown in Examples 10, 11 and 12. Maximum stabilizing effects were obtained at levels of 2.0–2.5% (percent of stabilizer solids in final slurry) and generally increased the recovery of viable cells of *L. sanfrancisco* by 3 to 6-fold over that obtained by freeze-drying without added stabilizer. As shown in Example 11, it was immaterial whether Hi heat or Low heat NFMS or dried cultured buttermilk solids were used and whether these solids (in aqueous suspension) were sterilized or not. Since the protein components in these various solids derived from non-fat milk varied in amount and condition, these results suggested that possibly other components were also involved in the stabilizing effect obtained. This was confirmed by the unexpected finding shown in Example 13 that, indeed, lactose (representing about 52% of NFMS) and another sugar, maltose, were definitely superior as stabilizers to NFMS when compared at the optimal level (2.5%) of the latter.

Other common stabilizers such as monosodium glutamate and Tween 80, used alone or in combination, were surprisingly even less beneficial than NFMS and were of no value or detrimental when used in conjunction with NFMS (Example 12).

(b) General Considerations

Percentage of stabilizer, as reported in this specification, pertains to the percentage by weight of the stabilizer solids in the final slurry containing said stabilizer before freeze-drying. The percentage of stabilizer solids in the final freeze-dried product was generally about 3.5–3.7 times that of the level in the slurry due, of course, to the concentration effect of drying (cf. Examples 10, 15, 16, 17, 18 and 19). This concentration factor varied slightly, however, with the concentration of stabilizer solids in its solution or suspension, and the ratio of flour:water in the culture slurry. Stabilizer solids could be added, in fact, as solids or as dilute or concentrated aqueous solutions or suspensions depending upon the rate and degree of dispersibility or solubility of the stabilizer solids and the desired viscosity of the final slurry. Obviously, to reduce freeze-drying costs it was desirable to add the stabilizer in the most concentrated form compatible with feasible processing characteristics and time.

In one study maltose was added at the 6% level to the flour:water slurry (1:2.5) as solids and as 50% and 25% solutions. Virtually identical quality of product was obtained with the viable counts/g being $1.4 \times 10^9$, $1.3 \times 10^9$, and $1.5 \times 10^9$, respectively (stab.-free basis). However, the stabilizer solids in the final product varied slightly being 18.9, 19.9 and 22.4%, respectively, representing concentration factors of 3.15, 3.33 and 3.73, respectively.

In general it was preferable to add the stabilizer solutions just prior to freeze-drying. In other words, if some holding time at the completion of the growth phase was necessary, as was almost always the case, stabilizer is best added at the end of the holding period as shown by the results of Example 14.

Sterilization of the stabilizer solutions or suspensions used in the process of the present invention was, in contrast to commercial pure culture starter culture production, generally unnecessary and of no value, particularly if these stabilizers represent commonly used baking ingredients.

(c) Carbohydrates or Carbohydrate-Rich Substances as Stabilizers

The finding that lactose was superior to NFMS at the 2.5% level (Example 13) was further developed by examining the effect of higher levels of lactose. Sweet whey solids (SWS) containing about 73% lactose (and about 12% protein) was used in lieu of lactose since it disperses much more readily than pure lactose which has limited degree and slow rate of solubility. As shown in Example 15, the beneficial stabilizing effect of SWS, as determined in two separate experiments, improved up to about 8% SWS and yielded 30–40% recovery of viable cells present prior to freeze-drying. This represents roughly a 40 to 50-fold improvement over that obtained by freeze-drying the flour slurry culture without added stabilizer and about a 10-fold further improvement over that achievable with the optimal level (2.5%) of NFMS. Of additional importance is the superior activity of the residual cells (rate of multiplication or acid production) obtained with the high level of SWS, as indicated by the substantial acid development (and presumed growth) in $3\frac{1}{2}$ hours in the activity test. As shown in Example 16, in two separate experiments lactose and sweet whey solids are, indeed, comparable in stabilizing effects, with the latter possibly being more consistent due to its more ready dispersibility.

The fact that sweet whey solids and other disaccharides improve their effectiveness with increasing level up to about 8%, whereas the effectiveness of NFMS decreases at levels over 2.5%, suggests that some of the protein components of the latter are deleterious when added to the flour system and thereby preclude using higher levels of NFMS as a source of lactose.

Other carbohydrates were examined as stabilizers, particularly those prominent in commonly used bakery ingredients such as sucrose, dextrose and maltose. Maltose, of course, is also a necessary carbohydrate for heavy growth of *L. sanfrancisco*. In Example 17 the effect of graded levels of maltose in two separate studies are shown and, similar to sweet whey solids, beneficial stabilizing effects improved with increasing level up to about 7.5% and yielded nearly 30% recovery of viable cells. Again these cells were very active, showing substantial acid development in $3\frac{1}{2}$ hours in the activity test.

In two side-by-side comparisons (Example 18) maltose and sweet whey solids were found to, indeed, be comparable and are considered superior or preferred stabilizers for the purposes of this invention. It is clear that any preparations that are high in lactose or maltose (preferably 70% or greater), such as certain non-diastatic malt syrups or solids or sweet or acid whey preparations, are included in this superior stabilizer category.

Sucrose was also found to be an effective stabilizer as shown in Example 19, although not quite as consistent as maltose or sweet whey solids. This may be related to problems encountered in rate of freezing sucrose-stabilized flour slurries or in a greater hygroscopicity in the product.

Prior art studies would not indicate that monosaccharides would be markedly inferior to disaccharides as stabilizers for freeze-drying lactic acid bacteria. However, as shown in Example 20, in the flour slurry system of the present invention the disaccharides (maltose, lactose or sweet whey solids and sucrose) were, surprisingly, roughly ten times as effective as the monosaccharides tested (glucose, galactose).

Of interest because of prior art practice of combining stabilizers was the finding that such commonly used stabilizers as NFMS or MSG were not beneficial and, in fact, detrimental when used in conjunction with a disaccharide (maltose) stabilizer (Example 21).

In selecting the optimal level of preferred stabilizers (i.e., those high in maltose or lactose) one has to consider not only the added drying costs but, more particularly, the point at which further improvement in recovery of viable cells is negated by increasing dilution with stabilizer solids. This generally occurred at a minimum of 6% or at a maximum of about 8% (percent of stabilizer solids in the final slurry). Accordingly, a level of 7.5% is selected as a recommended level which includes a slight safety factor above the minimal desired level.

In summary, the approximate optimal results obtained with various stabilizers under the modest freezing conditions employed (described later) from flour slurry cultures containing 1 to $2 \times 10^9$ cells per gram of *L. sanfrancisco* is as follows:

| Stabilizer | Viable count/g. in Freeze-dried prod. (stab.-free basis) | % recovery of *L. sanfran.* after freeze drying |
|---|---|---|
| None | $4 \times 10^7$ | 0.7 |
| 1.25% MSG or 0.1% Tween 80 | $1 \times 10^8$ | 1.5 |
| 2.5% NFMS or other milk solids | $2.5 \times 10^8$ | 3.7 |
| 2.5% Lactose, Maltose, SWS | 4 to $5 \times 10^8$ | 6.5 to 7 |
| 4.0% Lactose, Maltose, SWS or 6% Sucrose | 0.5 to $1 \times 10^9$ | 9 to 16 |
| 6.0% Lactose, Maltose, SWS or 7.5% Sucrose | 1 to $1.9 \times 10^9$ | 20 to 30 |
| 7.5 to 8.0% Maltose, SWS | 1.5 to $2.5 \times 10^9$ | 30 to 45 |

4. Freezing Conditions (prior to vacuum or freeze-drying)

As has long been known, rapid freezing is of vital importance in the preservation of the viability and activity of frozen or freeze-dried preparation of lactic acid and other bacteria. Commercially this is accomplished by the flash (immersion) freezing of small quantities (generally 4 oz. or less per container) or thin layers (¼ to ⅜″) in liquid nitrogen (approximately −300° F.) or dry ice-solvent mixtures (approximately −110° F.) or at very low (−60 to −80° F.) mechanically-produced temperatures. The higher the temperature or slower the freezing condition, the more critical becomes the need for stabilizers to prevent injury or death to the bacterial cells during freezing and/or freeze-drying. At liquid nitrogen immersion temperatures, small quantities (a few grams) of some bacterial species may even be flash frozen successfully without the use of any stabilizer. None of the above flash-freezing conditions, however, lend themselves to economically feasible large or industrial scale production.

A main thrust of the present invention is to complement its use of inexpensive large scale bakery type inocula and media with the use of conventional freezing facilities such as those used for various foods in the range of about −10° to −25° F. Two methods were used in the process of the present invention. In the first, a −25° F. frozen storage room with mild air circulation (just sufficient to implement temperature control) was employed. Approximately 180 ml. of flour slurry culture containing stabilizer, and at about 55° F., was placed on pre-chilled (to −25° F.) 8″ diameter aluminum pie pans giving a layer nearly ¼″ deep. Under these conditions the freezing point of the slurry (approximately 29° F.) was reached in 2½ to 3 minutes where it remained for an additional 5 minutes after which the temperature decreased steadily. After 25 minutes the temperature had dropped to −15° F. and the pan was transferred to the freeze dryer.

In the second and larger scale method a blast freezer operating at −15° F. and with a linear air flow of 500 ft./min. was employed (this is a comparatively modest condition as most blast freezers operate at −20° F. or below). 2000 ml. of flour slurry culture containing 6% sweet whey solids as stabilizer, and at 55° F., was transferred to a heavy gauge pre-chilled (to −15° F.) stainless steel tray approximately 35″×12″ giving a layer between ¼ and ⅜″ deep. Temperature decrease was measured by an indicating potentiometer as shown in Example 22 which is presented as a graph in FIG. 1. The freezing point of 29° F. was reached in about 3 minutes and remained at this temperature for about an additional 6 minutes, after which the temperature decreased steadily below freezing, a pattern very similar to that observed with the first smaller scale method. After 40 minutes the temperature had levelled off at about −15° F. and the tray was transferred to the freeze dryer. In this study, for comparative purposes some of the same slurry (180 ml.) was placed on the 8″ diameter aluminum pan in the −25° F. room. Both freezing methods yielded product with virtually identical counts of $2.1 \times 10^9$ per gram (stab.-free basis) representing recovery of approximately 38% of the viable bacteria present in the liquid slurry prior to freezing.

Beneficial to the process is the pre-chilling or conditioning of the aluminum or stainless steel (or other metals of good heat conductivity) trays. This pre-chilled contact surface and "cold reservoir" contributes vitally to extracting the heat rapidly from the flour slurries and permitting reaching the freezing point in about 3 minutes.

The other conditions in the freezing step permissible under the process of the present invention represent the interrelationships between temperature of slurry, temperature of contact surface, degree of air flow and thickness of layer. Generally, the modest conditions used throughout the development of the present invention, namely −10 to −25° F., represent an upper limit of the temperature variable which would be employed with reasonable thickness of layer (¼ to ⅜″). Obviously, more rapid freezing conditions could only improve the recovery and activity of the bacteria but are not essential to the success of this invention. By the same reasoning freezing could, indeed, take place directly on the shelves of those freeze-dryers capable of having their temperatures reduced to −25° F. or below. However, this is considered awkward, more costly and not as amenable to large scale production as blast freezers, cold storage rooms with air circulation, or tunnel or belt freezers or immersion freezing of drops in edible refrigerant.

In a separate and earlier study is was found that fairly rapid transfer to, or initiation of, freeze-drying may be highly desirable depending upon the temperature of the frozen slurry. As shown in Example 23, holding for 24 hours at −25° F. after freezing resulted in slight but significant loss in activity of the viable cells in the dried product which might be accommodated or tolerated. However, holding for 24 hours at −10° F. was highly damaging both to viable count and activity.

5. Drying Conditions

The vacuum drying phase of the freeze-drying process is not a novel feature of this invention and is selected to provide conditions compatible with achieving a viable bacterial product with good activity and stability. These conditions include obtaining a final moisture content of not over 4% (2% or less preferred) in the product and minimizing final product temperature reached during drying to 80° F. or lower (preferably 70° F. or lower). Any vacuum drying system capable of sufficiently rapid evacuation to prevent incipient thawing of the frozen flour slurry product placed in it and of maintaining a vacuum of 200 microns or less (preferably 100 microns or less) can be used. Obviously the better the vacuum the lower the final product temperature necessary to reach the desired moisture content of about 2%. Generally, in the process of the present invention the trays or pans containing layers of frozen slurry culture $\frac{1}{4}''$ to $\frac{3}{8}''$ in depth and at temperature generally below −10° F. were transferred to the shelves of the vacuum chamber and the drying completed in about 18 hours with the chamber pulling down to a vacuum of 50 to 100 microns. During the initial stages of vacuum drying, but not till after the vacuum had been established, heat exchange fluid (water or glycol) was pumped through the shelves at about 50° F. and "heat", i.e., shelf temperatures of 60°–80° F., was not applied until the last 8 to 12 hours of the 18 hour drying cycle.

The low moisture content of the product, i.e., approximately 2%, is essential to the stability of the bacteria in the product during subsequent storage, handling and distribution. One value of freeze-drying per se is its ability to achieve this critically essential low moisture level. Since the bacteria in the drying product, particularly during the later stages, are not stable at elevated temperatures the minimal finishing temperature (about 70° F.) is of obvious importance in achieving maximal quality in the initial product.

6. Retention of Lactic and Acetic Acids During Freeze-Drying

Lactic and acetic acids were determined in two different liquid flour slurry cultures and in the freeze-dried products derived therefrom according to a method previously described (Ng. H., "Factors Affecting Organic Acid Production By Sour Dough (San Francisco) Bacteria", Applied Microbiol. 23 1153-1159 (1972)). The average percentage retention of these acids after freeze-drying was 85% for lactic acid and 57% for acetic, the latter acid being, of course, more volatile. This finding that a substantial percentage (a majority or more than 50%) of these natural fermentation acids are retained during freeze-drying (along with the bacteria) is an added novel feature of the product of this invention which contributes both to the convenience and safety of the bakery process utilizing the product.

The percentage retention is made even more significant by the fact that acid production in a flour slurry culture per unit weight of flour is approximately twice that in a mother sponge or dough.

7. Stability of Freeze-Dried Product

One of the improvements represented by the present invention of much practical importance to the baker is to provide a product which can be held in quantities at above freezing temperatures for an adequate period of time (months). This is in contrast to the present frozen product of commerce which must be transported in small quantities in liquid nitrogen or dry ice and held by the baker is specially-procured freezers operating at −40° F. or lower.

Stability tests on the present product illustrated in Example 24 show good to excellent retention of viable count and activity for at least 10 weeks (not tested longer) at 37°–55° F., temperatures readily available to the baker as cooler or retarder boxes used to hold yeast and other materials. As expected, the activity deteriorated somewhat more rapidly than viable count. This translates into a slightly longer lag period of the first step of the application in the bakery.

These stability tests were carried out in screw-cap jars having a large air headspace. Further improvements in stability are possible by storage under reduced oxygen tension but are not necessary for the purposes of this invention.

As mentioned earlier, stability is dependent upon maintaining a low moisture content in the product—2% in the example shown. Obviously, suitable packaging impervious to moisture are helpful in distributing the product.

8. Superior Activity of the Present Freeze-Dried Product Over Commercial Products

(a) Demonstration of Superior Activity

The superior activity of the products of this invention over present commercial preparations of *L. sanfrancsisco* in terms of more rapid multiplication, acid production and shorter lag periods are readily demonstrated.

First, a comparison is made between the product of this invention and a commercial frozen preparation in Example 25 using only 1/10th as many cells (count) from the present product. As the results show, even with 1/10th the number of cells (initial count in assay mixture), the present product is equivalent or better than the commercial product. After 5½ hours of incubating the assay mixtures there has been no measurable multiplication in the commercial product while the cells from the present product have multiplied nearly ten times. Acid production (pH decrease) results, as a measure of comparative growth and activity, are even more striking. Thus, even after the counts have become equivalent after 5½ hours, the rate of acid production in the next 3½ hours is markedly greater with the present product.

A second method of comparison is shown in Example 26. Here the present product is compared at the same level of initial count in the assay mixture with commercial freeze-dried and frozen products in three different such comparisons. It is shown that, regardless of the initial count (varying between $6.5 \times 10^6$ and $7 \times 10^7$), at the 5½ hour period the cells from the present product have multiplied between 11 and 24 times while there has been virtually no multiplication of the cells from the 3 commercial preparations. Acid production comparisons show the superior activity of the present products in an even more striking manner.

Of additional noteworthy importance in Example 26 is the multiplication (4.4 to 7 times) and acid production exhibited by the present samples after only 3½ hours incubation of the assay mixtures.

(b) Reasons for Superior Activity of the Present Product

There are several possibilities for the superior activity of the product of this invention all of which may contribute including: (1) the cells have never been removed from their natural flour culture habitat thereby minimizing injury or shock during processing; (2) in using mother sponge as a seed or inoculum one is using many closely related strains of *L. sanfrancisco* thereby permitting a natural selection of superior strains for surviving freeze-drying; and (3) as will be demonstrated there are non-microbial factors carried over in transferring from a flour system which accelerate the growth of *L. sanfrancisco*.

First, examination of the data in Example 27 shows, for three different present preparations, that the greater the level used in the assay mixture, the more rapid the multiplication. Thus for A in Example 27, the highest level (7.0 grams) multiplied 24 times in 5½ hours; the next highest level (0.70 grams) fifteen times in 5½ hours; and the lowest level (0.28 grams) 9.4 times in 5½ hours. These results strongly indicate that the greater the level of flour-based culture used and the greater the carryover of non-microbial stimulatory factors, the greater the activity of the cells.

The above indication of stimulatory non-microbial factors was confirmed with the more sluggish commercial type preparation as shown in Example 28 where "dead" mother sponge was used as a source of flour-base culture without any viable *L. sanfrancisco* cells. Experience has shown that when large chunks of mother sponge are slowly frozen at 0° F. and held for several months at this temperature, the bacteria are virtually completely destroyed after 3 to 6 months. Thus, as shown in Example 28, supplementing a commercial freeze-dried preparation with "dead" mother sponge (Sample 3) roughly doubles the rate of growth and acid production as compared to the sample without the "dead" mother sponge (Sample 2). The data in the table also confirm that the "dead" mother sponge alone (Sample 1) has no activity.

It is further shown in Example 29 that none of the key nutrients developed for the synthetic broth growth medium (such as fresh yeast extractives, maltose, purines-pyrimidines or Tween 80) have a similar stimulatory effect and are, in fact, detrimental. Thus the nature of the stimulatory non-viable factors transmitted with a flour culture product are not known but must be considered another unique feature of the product of this invention.

9. Illustrative Examples of Bakery Application of the Present Freeze-Dried Product in San Francisco Sour Dough French Bread For convenience to those skilled in bakery practice, all of the formulae to be described involve approximately 100 lb. of flour per batch (actually 110 to 112 lb.) yielding 177 lb. of bread dough which, in turn, yields about 140 1 lb. loaves of bread per batch. This represents an amount of bread dough conveniently prepared in a small industrial scale horizontal mixer but is large enough to be readily translated into even larger scale production.

The usual steps of floor time after mixing, scaling, rounding, overhead proof, molding and final proof on canvas or boards have been described earlier and are applicable in the Examples to be described.

(a) 6 to 7 Hour Final Proof Process

As a reference point, attention is directed to Example 30 where the conventional San Francisco sour dough bread preparation, prepared on the above scale, is described. It is noted that the mother sponge (i.e., inoculum) contributes both the souring agent, *L. sanfrancisco*, and the leavening agent, the sour dough yeast, *T. holmii*. It also contributes about 11% (9 to 12) of the total flour in the bread dough formula which is the determining factor in yielding a bread dough which, after molding, requires 6 to 7 hour proof time before baking.

In Example 31 various procedures are shown for applying the freeze-dried starter product of this invention in formulations also designed for a 6 to 7 hour final proof period. Thus, in Example 31-A, 1 oz. (0.06 lb.) of the freeze-dried preparation is utilized in the first step only to build a sponge of the same type as conventional mother sponge (flour:water = 1:0.45). This sponge is then utilized in the second step which is the actual bread dough preparation at about the same level (11% of the total flour) described in the conventional process of Example 30. However, since this new sponge does not contain the sour dough yeast, *T. holmii*, the formulation is carefully modified to substitute Bakers yeast at a very low level = approximately 0.05% of the flour, consistent with a 6 to 7 hour proof.

It is necessary to digress at this point to underline that substituting Bakers yeast should be done with extreme caution and precision. Bakers yeast is a much more rapid and prolific gas producer than *T. homlii* which can lead to undesirable ballooning and thin crust bread. Moreover, Bakers yeast competes with *L. sanfrancisco* for the maltose formed in the dough (*T. holmii* does not utilize maltose) which can reduce both the acidity developed and lighten the crust color, the latter being dependent upon the maltose not utilized and its participation in the browning reaction. In the formulations devised the deleterious effects of Bakers yeast are controlled by: (1) very careful control of the level used; (2) the initial acidity and acidity developed, thus as the pH drops to 4.2 and lower the action of Bakers yeast is greatly retarded; and (3) by providing sucrose or glucose in the formulae where high levels of Bakers yeast are used to provide not only a maltose-sparing action but to provide rapid leavening in very short proof processes.

Continuing with the use of the freeze-dried starter in 6 to 7 hour final proof processes, Examples 31-B and 31-C illustrate its incorporation in liquid sponges (flour:water = 1:1 and 1:2.5) as the first step. Since these liquid sponges develop roughly twice the viable count and acid production per unit weight of flour as does the mother sponge type (flour:water = 1:0.45), they are introduced into the second step at a level of only 5.5% of the total flour (instead of 11%). The second step is again the preparation of the bread dough. Another difference is that since the liquid sponges contribute very little strength to the bread dough, use of dough strengtheners as, e.g., $KBRO_3$ or Ascorbic Acid are desirable. Alternately, higher gluten flour or lower water absorption may also be used to strengthen the bread dough.

Since economics as well as convenience are important, the bread yields obtained in the 6 to 7 hour proof processes are summarized in Example 31-D. It is seen that using a single step sponge preparation the estimated yield is 2300 1-lb. loaves per 1 lb. of freeze-dried starter and, using a 2-step sponge preparation (not shown but described), a yield of 20,000 1-lb. loaves of bread per 1 lb. of freeze-dried starter would be expected.

(b) Rapid (1½ hour) Final Proof Process

One of the factors limiting the wider adoption of the San Francisco sour dough French bread process in other areas is the 6 to 7 hour proof time required. Accordingly, special formulations designed to greatly shorten this proof time to 1½ hours or less utilizing the product of this invention have been developed.

The basic bread dough formulation designed to accomplish this is described in Example 32-A. Gross differences from the formuation used for the 6 to 7 hour proof process are shown as follows:

1. Sponge level is increased about 3-fold, i.e., to about 30-40% of the total flour in the formula.
2. Not only does this increase the level of inoculum of *L. sanfrancisco* by 3-fold but it also increases the initial acidification to a pH of 4.4-4.5 (instead of 5.3-5.4) which not only provides a headstart on sour developement but contributes vitally in controlling the bakers yeast activity.
3. Bakers yeast is greatly increased from 0.05% of the flour to about 1% (or 2.5-3% for a 1 hour proof process).
4. 1% sugar is added and is absolutely necessary for the bakers yeast to achieve the rapid leavening needed for the short proof process without affecting acidity production by *L. sanfrancisco*.

In Example 32-B1 are illustrated some 2-step procedures for preparation of the sponge used in the rapid proof process. Freeze-dried starter is, as before, added only in the first step. Three different type sponges are shown in the first step but all are converted to a mother sponge type (flour:water=1.0.45) for the second step. In Example 32-B2 are illustrated alternate 2-step procedures where the second step is a liquid sponge type (flour:water=1:1) and a modified bread dough formulation is shown to compensate for the higher water content of the sponge.

It is shown in Example 32-C that, using these 2-step procedures for the preparation of the sponge for the rapid proof process, approximately 3500 1-lb. loaves of bread are produced per 1 lb. of freeze-dried starter.

It is further shown in Example 32-D that a 1-step sponge preparation can be used, depending upon cost and convenience factors, to yield an estimated 550 to 778 1-lb. loaves of pread per 1 lb. of freeze-dried starter.

(c) General

It is apparent from the formulations illustrated that many different procedures may be used depending upon the final proof time desired, the type of equipment available and cost and convenience factors. Artificial acidification in the first step of sponge preparation reduces the amount of freeze-dried starter needed. However, as noted in Examples 31-D, 32-C and 32-D1, one can choose to increase the level of freeze-dried starter used so that artifical acidification is unnecessary with, however, significant reduction in yields.

EXAMPLE 1

LACK OF SUCCESS FREEZE-DRYING MOTHER SPONGE (DILUTED) DIRECTLY

A. Mother sponge containing $2.4 \times 10^9$ cells of *L. sanfrancisco* per g. diluted with water to give slurry having flour:water ratio of 1:2.5 as follows:

825 g. mother sponge
  (569 g. higluten flour + 256 g. water)
  1025 g. water
  1850 g. slurry containing $1.1 \times 10^9$ cells/g.

B. Compared with: Flour slurry culture (flour:water 1:2.5) as follows:

120 g. mother sponge
  600 g. higluten flour   Incubate: 8 hr. at 80° F. plus
  1500 g. water           2½ hr. at 55° F.
  13.2 g. salt
  2233.2 g. slurry        Final count = $2.4 \times 10^9$/g.

C. Relative Activity of Freeze-Dried Products from A and B:

| Sample | Viable Count/g. in Freeze-Dried Product (stab.-free basis) | Activity* pH decrease in 5½ hr. |
|---|---|---|
| A as is | $6.1 \times 10^6$ | .00 |
| A + 2.5% NFMS** | $7.9 \times 10^6$ | -.00 |
| A + 2.5% Maltose** | $3.1 \times 10^7$ | .05 |
| B as is | $6.7 \times 10^7$ | .07 |
| B + 2.5% NFMS** | $2.8 \times 10^8$ | .33 |
| B + 2.5% Maltose** | $4.9 \times 10^8$ | .44 |

*7.0 g. (stab.-free basis) used for all samples in activity test
**% of these stabilizer solids in final slurry

EXAMPLE 2

THE PRESENT FREEZE-DRIED PRODUCT COMPARED WITH MOTHER SPONGE AS SEED (INOCULUM)

A. The Present Product (count of $1.6 \times 10^9$/g.) as Seed

Step 1: 7.0g. (stab.-free) Present Product*
 50.0g. Higluten flour          Incubate 7 hr. at 80° F.
 125.0g. Water
 1.1g. Salt                      Initial: pH = 5.28
                                 Final: pH = 3.77 Count = $1.6 \times 10^9$/g

*Contributes 12.0% of total flour in Step 1

Step 2: 44g. from Step 1**       Incubate 7½ hr. at 80° F. + 2 hr. at 55° F.
 230g. Higluten flour
 535g. Water                     Initial: pH = 5.60 Count = $8.7 \times 10^7$/g.
 4.84g. Salt                     + 7½ hr.: pH = 3.78
                                 + 2 hr.: pH = 3.70 Count = $1.6 \times 10^9$/g.

**contributes 5.8% of total flour in Step 2

B. Mother Sponge as Seed

Step 1: 100g. Mother sponge      Incubate 6 hr. at 80° F.
 200g. Higluten flour
 90g. Water                      Initial: pH = 4.80
                                 Final: pH = 3.93 Count = $1.4 \times 10^9$/g.

| Step 2: | 44g. from Step 1::: | Incubate 7½ hr. at 80° F. + 2 hr. at 55° F. |
|---|---|---|
| | 220g. Highluten flour | |
| | 550g. Water | Initial: pH = 5.52 Count = 7.3 × $10^7$/g. |
| | 4.84g. Salt | + 7½ hr.: pH = 3.80 |
| | | + 2 hr.: pH = 3.72 Count = 1.2 × $10^9$/g. |

***Contributes 12.9% of total flour in Step 2

C. Activity of Freeze-Dried Prooducts from Step 2 in A and B above

| Sample | Viable count/g. in freeze-dried prod. (stab.-free basis) | % recovery* of L. sanfran. after freeze-drying | Activity** pH decrease in: 3.5 hr | 5.5 hr. | 7.5 hr |
|---|---|---|---|---|---|
| A as is | 2.1 × $10^7$ | 0.4 | .00 | .02 | .19 |
| A + 7.5% maltose*** | 1.1 × $10^9$ | 21.0 | .40 | 1.12 | 1.47 |
| B as is | 2.2 × $10^7$ | 0.6 | .00 | .05 | .29 |
| B + 7.5% maltose | 0.9 × $10^9$ | 21.0 | .43 | 1.13 | 1.44 |

*Calculated from counts in final slurry and freeze-dried product both on moisture-free basis
**7.0g. (stab-free basis) used for all samples in activity test
***% of maltose solids in final slurry

EXAMPLE 3

COMMERCIAL FREEZE-DRIED CULTURE OF
L. sanfrancisco AS SEED (INOCULUM)
VS.
MOTHER SPONGE OR THE PRESENT
FREEZE-DRIED PRODUCT AS SEEDS

| | Used As Inoculum | Stabilizer | Viable count/g. in freeze dried prod. (stab.-free basis) | Activity* pH decrease in 7½ hr. |
|---|---|---|---|---|
| A. | Commercial FD** | None | 3.4 × $10^7$ | .15 |
| | Commercial FD | 2.5% NFMS*** | 2.6 × $10^7$ | .08 |
| | Mother Sponge | None | 2.3 × $10^7$ | .43 |
| | Mother Sponge | 2.5% NFMS | 7.7 × $10^7$ | .73 |
| B. | Commercial FD | None | 8.2 × $10^7$ | .12 |
| | Commercial FD | 2.5% NFMS | 2.0 × $10^8$ | .42 |
| | Present FD | None | 5.1 × $10^7$ | .25 |
| | Present FD | 2.5% NFMS | 1.7 × $10^8$ | .84 |

*7.0g. (stab.-free basis) used for all samples in activity test
**FD = freeze-dried
***% of non-fat milk solids in final slurry

EXAMPLE 4

RECOVERY OF L. sanfrancisco FROM DOUGHS AND SLURRIES OF DIFFERENT WATER CONTENT*

| Flour:Water Ratio | Viable Count/g. in freeze-dried product |
|---|---|
| 1:0.45 (mother sponge) | <1 × $10^5$ |
| 1:1 | 5.4 × $10^6$ |
| 1:2.5 | 4.0 × $10^7$ |
| 1:5 | 2.2 × $10^6$ |
| 1:8.5 | <1 × $10^5$ |

*All were inoculated with mother sponge and developed at 80° F. to pH 3.9 ± 0.1. No stabilizers added. Frozen at −25° F. with mild air circulation in layers approximately ¼" deep.

EXAMPLE 5

COMPARISON OF FLOUR:WATER RATIOS
OF 1:2.5 AND 1:1 AS GROWTH MEDIA

A. Mother sponge used as seed:
   pH = 3.92 Count = 3.0 × $10^9$/g. (Count/g. flour = 4.3 × $10^9$)

B. Flour:Water - 1:2.5
   44g. Mother sponge  Incubate 7½hr. at 80° F. + 4 hr. at 55° F.
   220g. Higluten flour
   550g. Water    Initial: pH-5.49 Count = 1.6 × $10^8$g.
   4.84g. Salt    + 7½ hr.: pH = 3.77
                  + 4 hr.: pH = 3.70 Count = 2.1 × $10^9$/g.
                  (Count/g. flour = 7.3 × $10^9$)
                  Freeze-dry part with
                  6% Sweet Whey Solids (SWS)

C. Flour:Water - 1:1  Incubate 7½ hr. at 80° F. + 4 hr. at 55° F.
   44g. Mother sponge  Initial: pH-5.5 Count = 3.2 × $10^8$/g.
   220g. Higluten flour  + 7½ hr.: pH - 3.80
   220g. Water    + 4 hr.: pH-3.79 Count = 4.9 × $10^9$/g.
   2.0g. Salt     (Count/g. flour = 9.7 × $10^9$)
                  Freeze-dry part as is and part after
                  diluting to 1:2.5 as follows:
                  234g. above 1:1
                  165g. water
                  1.32g. salt
                  Use 6% Sweet Whey Solids with
                  this part D. Activity of Freeze-Dried Products from B and C above

| | Viable count/g in freeze-dried prod. (stab.-free basis) | % recovery* of L. sanfran. after freeze-drying | Activity** pH decrease in: 3.5 hr. | 5.5 hr. | 7.5 hr. | 9 hr. |
|---|---|---|---|---|---|---|
| 1:2.5 as is | 3.9 × 10 | 0.6 | .00 | .05 | .38 | .83 |
| 1:1 as is | 1.6 × $10^7$ | 0.2 | .00 | .00 | .07 | .28 |
| 1:2.5 + 6% SWS*** | 1.0 × $10^9$ | 15 | .29 | 1.04 | 1.07 | |
| 1:1 after diluted to 1:2.5 + 6% SWS | 1.0 × $10^9$ | 12 | .42 | 1.13 | 1.44 | |

*Calculated from counts in final slurry and freeze-dried product both on moisture-free basis
**7.0g. (stab.-free basis) used for all samples in activity test
***% pf Sweet Whey Solids in final slurry

EXAMPLE 6

COMPARISON OF FLOUR:WATER RATIOS OF
1:2.5 AND 1:1.5 AS GROWTH MEDIA

A. Mother sponge used as seed:
   pH = 4.00 Count = 2.5 × $10^9$/g. (Count/g. flour = 3.6 × $10^9$)

B. Flour:Water - 1:2.5
   44g. Mother sponge  Incubate 7 hr. at 80° F. + 3 hr. at 55° F.
   220g. Higluten flour
   550g. Water    Initial: pH = 5.50 Count = 1.3 × $10^8$/g.

-continued

**COMPARISON OF FLOUR:WATER RATIOS OF
1:2.5 AND 1:1.5 AS GROWTH MEDIA**

| | | |
|---|---|---|
| | 4.84g. Salt | 7 hr.: pH = 3.80 |
| | | 3 hr.: pH = 3.71 Count = 1.0 × 10$^9$/g. |
| | | Count/g. flour = 3.5 × 10$^9$) |
| | | Freeze-dry part as is and part with 8% maltose |
| C. | Flour:Water - 1:1.5 | |
| | 44g. Mother sponge | Incubate 7 hr. at 80° F. + 3 hr. at 55° F. |
| | 220g. Higluten flour | |
| | 330g. Water | Initial: pH = 5.53 Count = 1.8 × 10$^8$/g. |
| | 3g. Salt | 7 hr.: pH = 3.78 |
| | | 3 hr.: pH = 3.76 Count = 2.2 × 10$^9$/g. |
| | | (Count/g. flour = 5.6 × 10$^9$) |
| | | Freeze-dry part as is and part with 8% maltose |
| D. | Activity of Freeze-Dried Products from B and C above | |

| Sample | Viable count/g. in freeze-dried prod. (stab.-free basis) | % recovery* after freeze-drying | Activity** pH decrease in: 3.5hr. | 5.5hr. | 7.5hr. | 9hr. |
|---|---|---|---|---|---|---|
| 1:2.5 as is | 2.9 × 10$^7$ | 0.9 | — | .00 | .15 | .55 |
| 1:1.5 as is | 4.6 × 10$^7$ | 0.9 | — | .05 | .34 | .86 |
| 1:2.5 8% maltose*** | 1.4 × 10$^9$ | 45 | .47 | 1.12 | 1.42 | |
| 1:1.5 8% maltose*** | 1.5 × 10$^9$ | 30 | .50 | 1.15 | 1.46 | |

*Calculated from counts in final slurry and freeze-dried product both on moisture-free basis
**7.0g. (stab.-free basis) used for all samples in activity test
***% of maltose solids in final slurry

EXAMPLE 7

COMPARISON OF BREAD FLOURS FOR MEDIA*

| Type | | % Protein | Viable count/g. in freeze-dried prod. (stab.-free basis) | % recovery** of L. sanfran. after freeze-drying | Activity*** pH decrease in: 3.5 hr. | 5.5 hr. |
|---|---|---|---|---|---|---|
| A. | Higluten | 14.7 | 1.1 × 10$^9$ | 28 | .46 | 1.14 |
| | Regular | 12.1 | 3.0 × 10$^8$ | 8 | .16 | .77 |
| B | Higluten 1 | 14.7 | 1.3 × 10$^9$ | 25 | .65 | 1.25 |
| | Higluten 2 | 13.2 | 1.3 × 10$^9$ | 30 | .64 | 1.27 |
| | Regular | 11.1 | 5.8 × 10$^8$ | 18 | .41 | 1.22 |

*All flour media prepared with flour; water ratio = 1:2.5 7.5% maltose used as stabilizer in all samples (% by weight before freeze-drying)
**Calculated from counts in final slurry and freeze-dried product both on moisture-free basis
***7.0g. (stab.-free basis) used for all samples in activity test

EXAMPLE 9

**LACK OF BENEFIT FROM NEUTRALIZATION
DURING OR AT CLOSE OF CULTURE PERIOD**

| Additive | pH of flour culture (flour:water 1:2.5) | Viable count/g. in freeze-dried prod. (stab.-free basis) | Activity* pH decrease in: 9 hr. |
|---|---|---|---|
| None | 3.90 | 2.0 × 10$^7$ | .48 |
| 4N KOH 3× during incubation | 4.74 | 1.2 × 10$^7$ | .18 |
| 4N KOH after incubation | 4.74 | 0.9 × 10$^7$ | .13 |
| 5.5% NFMS after incubation | 4.90 | 3.6 × 10$^7$ | .76 |

*7.0g. (stab.-free basis) used for all samples in activity test

EXAMPLE 8

**STUDY OF TEMPERATURE-TIME CONDITIONS
FOR HOLDING FLOUR SLURRY CULTURE**

A. Mother sponge inoculum: pH = 4.03 Count = 2.4 × 10$^9$g. (Count/g. flour = 3.5 × 10$^9$)
B. Flour slurry culture* (flour:water = 1:2.5) and corresponding freeze-dried product

| Total elasped time (hr.) | Incubation temp. & time | Slurry pH | Slurry count/g. | Freeze-Dried Product count/g. | %** recovery | Activity*** pH decrease in: 5½ hr. | 7½ hr. |
|---|---|---|---|---|---|---|---|
| 0 | — | 5.53 | 1.3 × 10$^8$ | | | | |
| 7 | 7 hr. at 80° F. | 3.88 | 2.1 × 10$^9$**** | | | | |
| 8½ | +1½ hr. at 80° F. | 3.74 | 1.9 × 10$^9$ | 2.6 × 10$^8$ | 3.8 | .31 | 1.03 |
| NORMAL HARVEST TIME but held additionally: | | | | | | | |
| 13 | +4½ hr. at 55° F. | 3.72 | 1.6 × 10$^9$ | 3.4 × 10$^8$ | 5.9 | .32 | 1.03 |
| 17½ | +9 hr. at 55° F. | 3.70 | 2.0 × 10$^9$ | 3.3 × 10$^8$ | 4.6 | .36 | 1.04 |
| 32½ | +24 hr. at 55° F. | 3.72 | 1.9 × 10$^9$ | 2.3 × 10$^8$ | 3.4 | .15 | .64 |
| 13 | +4½ hr. at 80° F. | 3.67 | 1.4 × 10$^9$ | 3.5 × 10$^8$ | 7.1 | .23 | .85 |
| 17½ | +9 hr. at 80° F. | 3.62 | 1.4 × 10$^9$ | 1.6 × 10$^8$ | 3.2 | .02 | .22 |
| 32½ | +24 hr. at 80° F. | NA | NA | .05 × 10$^8$ | — | .00 | .00 |

*2.5% NFMS used as stabilizer on all samples. Added just after elapsed time and about 20 minutes prior to freeze-drying.
**Calculated from counts in slurry and freeze-dried product both on moisture-free basis
***7.0g. (stab.-free basis) used for all freeze-dried samples in activity test
****equals Count/g. flour of 7.4 × 10$^9$ (compare with that of mother sponge)

EXAMPLE 10

NON FAT MILK SOLIDS (NFMS) AS STABILIZERS*

| | Level of NFMS | | Viable count/g. in freeze-dried prod. (stab.-free basis) | Activity*** pH decrease in: | |
|---|---|---|---|---|---|
| | % in final slurry | % in freeze-dried product | | 5½ hr. | 7½ hr. |
| A. | 0 | 0 | $2.9 \times 10^7$ | .08 | .35 |
| | 2.5 | 9.4 | $1.2 \times 10^8$ | .41 | .97 |
| | 5.0 | 19.6 | $5.2 \times 10^7$ | .15 | .55 |
| | 7.5 | 30.4 | $0.6 \times 10^7$ | .04 | .28 |
| B. | 1.0 | 3.7 | $6.6 \times 10^6$ | .09 | .43 |
| | 2.0 | 7.5 | $9.3 \times 10^7$ | .20 | .90 |
| | 3.0 | 10.5 | $7.2 \times 10^7$ | .15 | .65 |
| | 4.0 | 15.4 | $5.8 \times 10^7$ | .15 | .66 |
| | 5.0 | 19.6 | $5.3 \times 10^7$ | .13 | .65 |

*NFMS added as 20% sterilized suspension
**Flour slurry of 1:2.5 flour:water ratio used as culture
***7.0g. (stab.-free basis) used for all samples in activity test

EXAMPLE 11

NFMS AND RELATED SUBSTANCES STABILIZERS ± STERILIZATION*

| Stabilizer | Level in final slurry | Viable count/g. freeze-dried prod. (stab.-free basis) | Activity pH decrease in: | |
|---|---|---|---|---|
| | | | 5½ hr. | 7½ hr. |
| Low Heat NFMS sterilized | 2.5% | $1.9 \times 10^8$ | .27 | .96 |
| Low Heat NFMS not sterilized | 2.5% | $2.0 \times 10^8$ | .20 | .87 |
| Hi Heat NFMS sterilized | 2.5% | $1.0 \times 10^8$ | .15 | .63 |
| Hi Heat NFMS not sterilized | 2.5% | $1.2 \times 10^8$ | .19 | .75 |
| Spray Dried Cultured Buttermilk Solids sterilized | 2.5% | $2.1 \times 10^8$ | .22 | .85 |
| Buttermilk Solids-not steril. | 2.5% | $2.0 \times 10^8$ | .17 | .77 |

*Footnotes as in Example 10 except for optional sterilization

EXAMPLE 12

MONOSODIUM GLUTAMATE (MSG), TWEEN 80, AND NFMS AS STABILIZERS*

| Stabilizer and % in final slurry | Viable count/g. in freeze-dried prod. (stab.-free basis) | % recovery** of L. sanfran. after freeze-drying | Activity*** pH decrease in: | |
|---|---|---|---|---|
| | | | 5½ hr. | 7½ hr. |
| A. MSG | | | | |
| 0 | $3.8 \times 10^7$ | 0.7 | | .40 |
| 0.5 | $7.8 \times 10^7$ | 1.4 | | .59 |
| 1.25 | $8.2 \times 10^7$ | 1.5 | | .70 |
| 2.00 | $5.7 \times 10^7$ | 1.1 | | .59 |
| B. Tween 80 ± MSG | | | | |
| 0 | $1.1 \times 10^7$ | 0.3 | | .30 |
| 0.1% TW 80 | $1.7 \times 10^7$ | 0.5 | | .52 |
| 1.25% MSG | $1.8 \times 10^7$ | 0.5 | | .60 |
| 0.1% TW 80 + 1.25% MSG | $1.4 \times 10^7$ | 0.4 | | .60 |
| C. NFMS ± MSG ± TW 80 | | | | |
| 0 | $9.6 \times 10^7$ | NA | .11 | .38 |
| 2.5% NFMS | $2.3 \times 10^8$ | NA | .38 | 1.19 |
| 2.5% NFMS + 1.7% MSG | $1.7 \times 10^8$ | NA | .31 | .99 |
| 2.5% NFMS + 0.6% TW 80 | $0.9 \times 10^8$ | NA | .32 | 1.05 |
| 1.7% MSG + 0.6% TW 80 | $1.5 \times 10^8$ | NA | .24 | .98 |

*Flour slurry of 1:2.5 flour:water ratio used as culture; MSG added as 33% solution; Tween 80 as 10% solution; NFMS as 20% suspension (not sterilized)
**Calculated from counts in final slurry and freeze-dried product both on moisture-free basis
***7.0g. (stab.-free basis) used for all samples in activity test

EXAMPLE 13

NFMS vs. LACTOSE AND MALTOSE AS STABILIZERS*

| Stabilizer and % in final slurry | Viable count/g. in freeze-dried prod. (stab.-free basis) | % recovery** of L. sanfran. after freeze-drying | Activity*** pH decrease in | |
|---|---|---|---|---|
| | | | 5½ hr. | 7½ hr. |
| None | $6.7 \times 10^7$ | 0.9 | .07 | .20 |
| 2.5% NFMS | $2.8 \times 10^8$ | 3.8 | .33 | 1.03 |
| 2.5% Lactose | $5.0 \times 10^8$ | 6.7 | .38 | 1.05 |
| 2.5% Maltose | $4.8 \times 10^8$ | 6.5 | .44 | 1.15 |

*Flour slurry of 1:2.5 flour:water ratio used as culture NFMS and Maltose added as 20% non-sterilized solution or suspension; Lactose added as 16.6% solution
**Calculated from counts in final slurry and freeze-dried product both on moisture-free basis
***7.0g. (stab.-free basis) used for all samples in activity test

EXAMPLE 14

TIME OF ADDITION OF STABILIZER SOLIDS*

| Stabilizer and time of addition | Viable count/g. in freeze-dried prod. (stab.-free basis) | % recovery** of L. sanfran. after freeze-drying |
|---|---|---|
| None | $3.9 \times 10^7$ | 0.4 |
| Slurry held 6 hr. at 55° F. with 2.5% NFMS already added | $2.8 \times 10^8$ | 2.6 |
| Slurry held 6 hr. at 55° F. before 2.5% NFMS added | $3.9 \times 10^8$ | 3.6 |

*Flour slurry of 1:2.5 flour:water ratio used as culture; NFMS added as 20% non-sterilized suspension
**Calculated from counts in final slurry and freeze-dried product both on a moisture-free basis

EXAMPLE 15

INCREASING LEVELS OF SWEET WHEY SOLIDS (SWS) AS STABILIZER*

| Level of SWS | | Viable count/g. in freeze-dried prod. (stab.-free basis) | % recovery*** of L. sanfran. | Activity**** pH decrease in: | | |
|---|---|---|---|---|---|---|
| % in final slurry** | % in freeze-dried product | | | 3.5hr. | 5.5hr. | 7.5hr. |
| A. 0 | 0 | $6.0 \times 10^7$ | 1.0 | .00 | .08 | .29 |
| 2.0 | 7.5 | $3.7 \times 10^8$ | 5.9 | .12 | .54 | 1.24 |
| 4.0 | 14.9 | $1.0 \times 10^9$ | 16.4 | .25 | .92 | 1.44 |
| 6.0 | 22.4 | $1.9 \times 10^9$ | 30.6 | .44 | 1.16 | 1.52 |
| B. 6.0 | 22.4 | $1.6 \times 10^9$ | 21.3 | .44 | 1.12 | |
| 8.0 | 30.1 | $2.4 \times 10^9$ | 38.2 | .50 | 1.15 | |
| 10.0 | 37.8 | $2.6 \times 10^9$ | 40.6 | .50 | 1.14 | |

*SWS added as 25% suspension
**Flour slurry of 1:2.5 flour:water ratio used as culture
***Calculated from counts in final slurry and freeze-dried product both on a moisture-free basis
****7.0g. (stab.-free basis) used for all samples in activity test

EXAMPLE 16

LACTOSE vs. SWEET WHEY SOLIDS (SWS) AS STABILIZERS

| Stabilizer and level | Viable | | | Activity*** | |
|---|---|---|---|---|---|
| % in final slurry** | % in freeze-dried product | count/g. in freeze-dried prod. (stab.-free basis) | % recovery*** of L. sanfran. | pH decrease in: | |
| | | | | 3½hr. | 5½hr. |
| A. | | | | | |
| Lactose: 6.0 | 22.4 | $1.6 \times 10^9$ | NA | .40 | 1.13 |
| SWS: 6.0 | 22.4 | $2.4 \times 10^9$ | NA | .59 | 1.26 |
| B. | | | | | |
| Lactose: 7.5 | 28.1 | $1.2 \times 10^9$ | 31.1 | .48 | 1.11 |
| SWS: 7.5 | 28.1 | $1.2 \times 10^9$ | 31.3 | .50 | 1.19 |

*Both added as 25% suspensions
**Flour Slurry of 1:2.5 flour:water ratio used as culture
***Calculated from counts in final slurry and freeze-dried product both on a moisture-free basis
****7.0g. (stab.-free basis) used for all samples in activity test

EXAMPLE 17

INCREASING LEVELS OF MALTOSE AS STABILIZER*

| Level of maltose | | Viable count/g. in freeze-dried prod. (stab.-free basis) | % recovery*** of L. sanfran. | Activity**** pH decrease in: | |
|---|---|---|---|---|---|
| % in final slurry** | % in freeze-dried product | | | 3½ hr. | 5½ hr. |
| A. 1.0 | 3.7 | $1.4 \times 10^8$ | 1.9 | NA | .10 |
| 2.0 | 7.5 | $3.3 \times 10^8$ | 4.2 | NA | .31 |
| 3.0 | 10.5 | $4.8 \times 10^8$ | 6.2 | NA | .48 |
| 4.0 | 15.4 | $7.7 \times 10^8$ | 9.0 | NA | .77 |
| B. 0 | 0 | $1.7 \times 10^7$ | 0.4 | .00 | .01 |
| 4.5 | 16.0 | $6.6 \times 10^8$ | 15.9 | .31 | 1.01 |
| 6.0 | 21.1 | $1.1 \times 10^9$ | 25.3 | .48 | 1.17 |
| 7.5 | 26.1 | $1.1 \times 10^9$ | 27.5 | .55 | 1.19 |
| 9.0 | 31.0 | $1.1 \times 10^9$ | 25.8 | .59 | 1.23 |

*Maltose added as 20% solution in A and 33% solution in B
**Flour slurry of 1:2.5 flour:water ratio used as culture
***Calculated from counts in final slurry and freeze-dried product both on a moisture-free basis
****7.0g. (stab.-free basis) used for all samples in activity test

EXAMPLE 18

MALTOSE vs. SWEET WHEY SOLIDS (SWS) AS STABILIZERS*

| Stabilizer | Level of stabilizer | | Viable count/g. in freeze-dried prod. (stab.-free basis) | % recov.*** of L. sanfran. | Activity**** pH decrease | |
|---|---|---|---|---|---|---|
| | in final slurry* | % in freeze-dried prod. | | | 3.5 hr | 5.5 hr. |
| A. | | | | | | |
| SWS | 8.0 | 30.1 | $2.4 \times 10^9$ | 38.2 | .50 | 1.15 |
| Maltose | 8.0 | 30.1 | $1.9 \times 10^9$ | 30.0 | .55 | 1.20 |
| B. | | | | | | |
| SWS | 7.5 | 28.1 | $1.2 \times 10^9$ | 31.3 | .50 | 1.19 |
| Maltose | 7.5 | 28.1 | $1.3 \times 10^9$ | 32.9 | .61 | 1.21 |

*Both added as 25% solution or suspension
**Flour flurry of 1:2.5 flour:water ratio used as culture
***Calculated from counts in final slurry and freeze-dried product both on a moisture-free basis
****7.0g. (stab.-free basis) used for all samples in activity test

EXAMPLE 19

SUCROSE AS STABILIZER*

| Stabilizer | Level of stabilizer | | Viable count/g. in freeze-dried prod. (stab.-free basis) | % recov.*** of L. sanfran. | Activity**** pH decrease | |
|---|---|---|---|---|---|---|
| | % in final slurry** | % in freeze-dried prod. | | | 3.5hr. | 5.5hr. |
| A. Sucrose | 0 | 0 | $3.3 \times 10^7$ | NA | .00 | .02 |
| Sucrose | 3.0 | 11.2 | $1.5 \times 10^8$ | NA | .04 | .21 |
| Sucrose | 4.5 | 16.7 | $3.6 \times 10^8$ | NA | .07 | .36 |
| Sucrose | 6.0 | 22.4 | $7.1 \times 10^8$ | NA | .24 | .76 |
| B. Sucrose | 4.0 | 14.9 | $4.2 \times 10^8$ | 5.7 | .13 | .61 |
| Maltose | 4.0 | 14.9 | $6.5 \times 10^8$ | 8.9 | .21 | .80 |

-continued

SUCROSE AS STABILIZER*

| Stabilizer | Level of stabilizer % in final slurry** | Level of stabilizer % in freeze-dried prod. | Viable count/g. in freeze-dried prod. (stab.-free basis) | % recov.*** of L. sanfran. | Activity**** pH decrease 3.5hr. | Activity**** pH decrease 5.5hr. |
|---|---|---|---|---|---|---|
| C. Sucrose | 6.0 | 22.4 | $1.0 \times 10^9$ | NA | .39 | 1.11 |
| Maltose | 6.0 | 22.4 | $1.4 \times 10^9$ | NA | .43 | 1.14 |
| D. Sucrose | 7.5 | 28.1 | $1.0 \times 10^9$ | 25.3 | .59 | 1.20 |
| Sweet WS | 7.5 | 28.1 | $1.2 \times 10^9$ | 31.3 | .50 | 1.19 |
| Maltose | 7.5 | 28.1 | $1.3 \times 10^9$ | 32.9 | .61 | 1.21 |

*Sucrose and other stabilizers added as 25% solutions or suspensions
**Flour slurry of 1:2.5 flour:water ratio used as culture
***Calculated from counts in final slurry and freeze-dried product both on a moisture-free basis
****7.0g. (stab.-free basis) used for all samples in activity test

EXAMPLE 20

SUPERIORITY OF DISACCHARIDES OVER MONOSACCHARIDES AS STABILIZERS*

| Stabilizer and level in final slurry** | viable count/g. in freeze-dried prod. (stab.-free basis) | Activity*** pH decrease in: 3.5 hr. | Activity*** pH decrease in: 5.5 hr. |
|---|---|---|---|
| A. 6% Glucose | $1.0 \times 10^8$ | .00 | .18 |
| 6% Sucrose | $1.0 \times 10^9$ | .39 | 1.11 |
| 6% Maltose | $1.4 \times 10^9$ | .43 | 1.14 |
| B. 6% Glucose | $2.1 \times 10^8$ | .03 | .41 |
| 6% Galactose | $3.4 \times 10^8$ | .15 | .77 |
| 6% Lactose | $1.6 \times 10^9$ | .40 | 1.13 |
| 6% Sweet Whey solids | $2.4 \times 10^9$ | .59 | 1.26 |

*Both monosaccharides (glucose, galactose) and disaccharides (sucrose, maltose, lactose, sweet whey solids) added as 25% solutions or suspensions
**Flour slurry of 1:2.5 flour:water ratio used as culture
***7.0g. (stab.-free basis) used for all samples in activity test

EXAMPLE 21

MALTOSE ± NFMS ± MONOSODIUM GLUTAMATE AS STABILIZERS*

| Stabilizer and % in final slurry** | Viable count/g. in freeze-dried prod. (stab.-free basis) | % recovery*** of L. sanfran. after freeze drying | Activity**** pH decrease in: 3.5hr. | Activity**** pH decrease in: 5.5hr. |
|---|---|---|---|---|
| 4% Maltose | $4.6 \times 10^8$ | 9.3 | .27 | .96 |
| 6% Maltose | $1.1 \times 10^9$ | 23.0 | .41 | 1.12 |
| 4% Maltose + 2% NFMS | $4.3 \times 10^8$ | 8.7 | .23 | .85 |
| 4% Maltose + 2% MSG | $4.2 \times 10^8$ | 8.5 | .05 | .57 |

*All stabilizers added as 25% solutions or supensions
**Flour slurry of 1:2.5 flour:water ratio used as culture
***Calculated from counts in final slurry and freeze-dried product both on a moisture-free basis
****7.0g. (stab.-free basis) used for all samples in activity test

EXAMPLE 23

HOLDING AFTER FREEZING AND BEFORE FREEZE-DRYING*

| Sample | Viable count/g. in freeze-dried prod. (stab.-free basis) | Activity** pH decrease in: 5.5 hr. | Activity** pH decrease in: 7.5 hr. |
|---|---|---|---|
| No stabilizer - freeze-dried immediately | $6.7 \times 10^7$ | .07 | .20 |
| 2.5% NFMS - freeze-dried immediately | $2.8 \times 10^8$ | .32 | 1.02 |
| 2.5% NFMS - held 24 hr. at −25° F. before freeze-drying | $2.7 \times 10^8$ | .23 | .80 |
| 2.5% NFMS - held 24 hr. at −10° F. before freeze-drying | $1.1 \times 10^8$ | .07 | .23 |

*Flour slurry culture of flour:water ratio of 1:2.5 used; frozen in ¼" layers on pre-chilled aluminum pans in −25° F. room with mild circulation
**7.0g. (stab.-free basis) used for all samples in activity test

EXAMPLE 24

STABILITY OF FREEZE-DRIED PRODUCT AT VARIOUS TEMPERATURES*

| | Time of Storage (weeks) | Temperature of storage 0° F. | 37° F. | 55° F. | 75° F. |
|---|---|---|---|---|---|
| A. Viable counts per g. | 0 | $1.8 \times 10^8$ | $1.8 \times 10^8$ | $1.8 \times 10^8$ | $1.8 \times 10^8$ |
| | 4½ | $2.4 \times 10^8$ | $1.9 \times 10^8$ | $1.7 \times 10^8$ | $5.5 \times 10^7$ |
| | 10 | $2.3 \times 10^8$ | $1.7 \times 10^8$ | $1.2 \times 10^8$ | $1.1 \times 10^7$ |
| | 16 | $1.8 \times 10^8$ | — | — | — |
| B. Activity: pH decrease in 7½ hr. | 0 | .88 | .88 | .88 | .88 |
| | 4½ | .94 | .73 | .69 | .30 |
| | 10 | .84 | .67 | .49 | .08 |
| | 16 | .83 | — | — | — |
| | | 0° F. count act.** | 37° F. count act.** | 55° F. count act.** | 75° F. count act.** |
| C. % retention after: (weeks) | 4½ | 100  100 | 100  83 | 94  78 | 30  38 |
| | 10 | 100  96 | 94  76 | 66  56 | 6  9 |
| | 16 | 100  94 | — | — | — |

*Flour:slurry culture of flour:water = 1:2.5 used and stabilized with 2.5% NFMS. Viable counts/g. are on a stabilizer-free basis. 7.0g. (stab.-free basis) of all samples used in activity test. Product contained 2.0% water
**activity

EXAMPLE 25

EQUIVALENCE OF THE PRESENT FREEZE-DRIED PRODUCT TO COMMERCIAL FROZEN SAMPLE AT 1/10th THE INITIAL COUNT*

| Time (hours) | Commercial Frozen B pH decrease | Commercial Frozen B Viable count per ml. | Commercial Frozen B Multiplication | Present Freeze-Dried pH decrease | Present Freeze-Dried Viable count per ml. | Present Freeze-Dried Multiplication |
|---|---|---|---|---|---|---|
| 0 | — | $2.9 \times 10^7$ | — | — | $2.7 \times 10^6$ | — |
| 3½ | 0 | | | 0 | $4.3 \times 10^6$ | (1.6 ×) |
| 5½ | .01 | $2.4 \times 10^7$ | 0 | .07 | $2.6 \times 10^7$ | (9.4 ×) |
| 7½ | .10 | $6.6 \times 10^7$ | (2.3 ×) | .51 | | |

EXAMPLE 26

SUPERIOR ACTIVITIES OF PRESENT FREEZE-DRIED PREPARATIONS TO COMMERCIAL PREPARATIONS WHEN COMPARED AT THE SAME INITIAL COUNT*

A. Initial counts in assay mixture = approx. $6.5 \times 10^6$ per ml.

| | Commercial Freeze-Dried A | | | Present Freeze-Dried | | |
|---|---|---|---|---|---|---|
| Time (hours) | pH decrease | Viable count per ml. | Multi-plication | pH decrease | Viable count per ml. | Multi-plication |
| 0 | — | $6.5 \times 10^6$ | — | — | $6.6 \times 10^6$ | — |
| 5½ | 0 | $6.5 \times 10^6$ | 0 | .38 | $7.0 \times 10^7$ | (11 ×) |
| 7½ | .04 | | | 1.08 | | |
| 10½ | .84 | | | 1.66 | | |
| 11 | | $6.3 \times 10^8$ | (98 ×) | | $1.5 \times 10^9$ | (227 ×) |

B. Initial counts in assay mixture = approx. $2.7 \times 10^7$ per ml.

| | Commercial Frozen B | | | Present Freeze-Dried | | |
|---|---|---|---|---|---|---|
| Time (hours) | pH decrease | Viable count per ml. | Multi-plication | pH decrease | Viable count per ml. | Multi-plication |
| 0 | — | $2.9 \times 10^7$ | — | — | $2.5 \times 10^7$ | — |
| 3½ | 0 | | | .19 | $1.1 \times 10^8$ | (4.4 ×) |
| 5½ | .01 | $2.4 \times 10^7$ | 0 | 1.01 | $3.3 \times 10^8$ | (13.2 ×) |
| 7½ | .10 | $6.6 \times 10^7$ | (2.3 ×) | 1.45 | | |
| 9 | .32 | | | 1.59 | $1.0 \times 10^9$ | (40.0 ×) |
| 10½ | .80 | | | | | |
| 12 | 1.24 | $1.3 \times 10^9$ | (44.8 ×) | | | |

C. Initial counts in assay mixture = $7 \times 10^7$ per ml.

| | Commercial Frozen B | | | Present Freeze-Dried | | |
|---|---|---|---|---|---|---|
| Time (hours) | pH decrease | Viable count per ml. | Multi-plication | pH decrease | Viable count per ml. | Multi-plication |
| 0 | — | $7.2 \times 10^7$ | — | — | $6.9 \times 10^7$ | — |
| 3½ | 0 | | | .56 | $4.6 \times 10^8$ | (7 ×) |
| 5½ | .11 | $10.1 \times 10^7$ | (1.4 ×) | 1.23 | $1.6 \times 10^9$ | (24 ×) |
| 7½ | .42 | | | 1.49 | | |
| 9 | .94 | | | 1.56 | $2.2 \times 10^9$ | (32 ×) |
| 10½ | 1.30 | | | | | |
| 12 | 1.55 | $2.2 \times 10^9$ | (31 ×) | | | |

*Usual assay mixture. Lactic:acetic (2%) 7:3 added where necessary to pH 5.4 ± 0.1.pH decrease and viable counts measured on assay mixture.

EQUIVALENCE OF THE PRESENT FREEZE-DRIED PRODUCT TO COMMERCIAL FROZEN SAMPLE AT 1/10th THE INITIAL COUNT*

| | Commercial Frozen B | | | Present Freeze-Dried | | |
|---|---|---|---|---|---|---|
| Time (hours) | pH decrease | Viable count per ml. | Multi-plication | pH decrease | Viable count per ml. | Multi-plication |
| 9 | .32 | | | 1.09 | | |
| 10½ | .80 | | | 1.46 | | |
| 12 | 1.24 | $1.3 \times 10^9$ | (45 ×) | 1.63 | $1.4 \times 10^9$ | (518×) |

*Usual assay mixture with:
0.50g. Comm. Frozen B + 3.6ml. 2% Lactic:Acetic 7:3 to give initial pH = 5.40
0.28g. present product (stab.-free basis) + 3.6ml. 2% Lactic:Acetic 7:3 to give initial pH = 5.40
pH decrease and viable counts (and multiplication) measured on assay mixture.

EXAMPLE 27

INCREASING RATE OF MULTIPLICATION WITH INCREASING LEVEL OF THE PRESENT FREEZE-DRIED PRODUCT USED IN ASSAY TEST*

A. Present product preparation stabilized with 8% SWS and containing $1.7 \times 10^9$/g. (stab.-free basis)

| | Weight (stab.-free basis) used in assay test | | | | | |
|---|---|---|---|---|---|---|
| | 7.0g. | | 0.70g. | | 0.28g. | |
| Time (hr.) | Viable count per ml. | Multi-plication | Viable count per ml. | Multi-plication | Viable count per ml. | Multi-plication |
| 0 | $6.9 \times 10^7$ | — | $6.9 \times 10^6$ | — | $2.7 \times 10^6$ | — |
| 3½ | $4.6 \times 10^8$ | (7 ×) | $1.3 \times 10^7$ | (1.9 ×) | $4.3 \times 10^6$ | (1.6 ×) |
| 5½ | $1.64 \times 10^9$ | (24 ×) | $1.03 \times 10^8$ | (15 ×) | $2.6 \times 10^7$ | (9.4 ×) |
| 9 | $2.17 \times 10^9$ | (32 ×) | | | | |
| 12 | | | $1.63 \times 10^9$ | (236 ×) | $1.43 \times 10^9$ | (518 ×) |

B. Present product preparation stabilized with 4% Maltose and containing $7.7 \times 10^8$/g. (stab.-free basis)

| | Weight (stab.-free basis) used in assay test | | | | | |
|---|---|---|---|---|---|---|
| | 7.0g. | | 1.75g. | | 0.35g. | |
| Time (hr.) | Viable count per ml. | Multi-plication | Viable count per ml. | Multi-plication | Viable count per ml. | Multi-plication |
| 0 | $2.48 \times 10^7$ | — | $6.20 \times 10^6$ | — | $1.24 \times 10^6$ | — |

-continued

INCREASING RATE OF MULTIPLICATION WITH INCREASING LEVEL OF THE PRESENT FREEZE-DRIED PRODUCT USED IN ASSAY TEST*

| 4   | $1.12 \times 10^8$ | $(4.5 \times)$  | $1.69 \times 10^7$ | $(2.7 \times)$ |                    |                |
|-----|--------------------|-----------------|--------------------|----------------|--------------------|----------------|
| 5½  | $3.24 \times 10^8$ | $(13.1 \times)$ | $6.13 \times 10^7$ | $(9.8 \times)$ | $7.13 \times 10^6$ | $(5.8 \times)$ |
| 9   | $1.00 \times 10^9$ | $(40 \times)$   |                    |                |                    |                |
| 11  |                    |                 | $1.23 \times 10^9$ | $(198 \times)$ |                    |                |
| 12  |                    |                 |                    |                | $8.50 \times 10^8$ | $(686 \times)$ |

C. Present product preparation stabilized with 2.5% NFMS and containing $2.7 \times 10^8$/g. (stab.-free basis)

| | Weight (stab.-free basis) used in assay test | | | |
|---|---|---|---|---|
| | 7.0g. | | 2.27g. | |
| Time (hr.) | Viable count per ml. | Multi-plication | Viable count per ml. | Multi-plication |
| 0 | $1.07 \times 10^7$ | — | $4.06 \times 10^6$ | — |
| 6 | $8.10 \times 10^7$ | $(7.6 \times)$ | $1.48 \times 10^7$ | $(3.7 \times)$ |

*Usual assay mixture. 2% Lactic:Acetic 7:3 added where necessary for initial pH adjustment.
pH decrease and viable counts measured on assay mixture.

EXAMPLE 28

**STIMULATORY EFFECT OF "DEAD"* MOTHER SPONGE ON ACTIVITY OF COMMERCIAL FREEZE-DRIED PREPARATION**

| | Sample 1: 10g. "dead" mother sponge used in assay (= blank) | | | Sample 2: 0.25g. Commercial FD** prep. used in assay | | | Sample 3: 0.25g. Commercial FD** prep +10g. "dead" mother sponge used in assay | | |
|---|---|---|---|---|---|---|---|---|---|
| Time (hr.) | pH decrease | Viable count | Multi-plicat. | pH decrease | Viable count | Multi-plicat. | pH decrease | Viable count | Multi-plicat. |
| 0   | —  | $<1 \times 10^4$ | —  | —   | $1.42 \times 10^7$ | —             | —    | $1.46 \times 10^7$ | —             |
| 5½  | 0  |                  |    | .05 |                    |               | .11  |                    |               |
| 7½  | 0  | $<1 \times 10^4$ | 0  | .34 | $3.16 \times 10^8$ | $(22\times)$  | .54  | $6.26 \times 10^8$ | $(43\times)$  |
| 9   | 0  |                  |    | .84 |                    |               | 1.10 |                    |               |

*Mother sponge held for over 1 year at 0° F. in large chunk; "no" ($<1 \times 10^4$) viable cells of *L. sanfrancisco* remaining
Sample 1: no acidification necessary. Initial pH of assay mixture = 5.54
Sample 2: acidified with 3.5 ml. 2% Lactic:acetic 7:3. Initial pH = 5.54
Sample 3: no acidification necessary. Initial pH of assay mixture = 5.52
**FD = freeze-dried

EXAMPLE 29

**INABILITY OF KEY NUTRIENTS* TO SUBSTITUTE FOR "DEAD" MOTHER SPONGE**

| Time (hr.) | 0.25 g. Commercial FD | 0.25 g. Commercial FD + 0.5% FYE | 0.25 g. Commercial FD + 1.0% Maltose | 0.25 g. Commercial FD + 0.1% Tween 80 + 0.5 ml. PP |
|---|---|---|---|---|
| | pH decrease in: | | | |
| 0   | —   | —   | —   | —   |
| 5½  | .04 | .00 | .00 | .03 |
| 7½  | .39 | .25 | .22 | .30 |
| 9   | .83 | .69 | .57 | .70 |

*Key nutrients include:
FYE = fresh yeast extractives
PP = purine-pyrimidine solution
described in:
Leo Kline and T.F. Sugihara "Microorganisms of the S.F. Sour Dough Bread Process" II. Applied Microbiol. 21, 459–465 (1971).

EXAMPLE 30

CONVENTIONAL SAN FRANCISCO SOUR DOUGH BREAD FORMULATION (6 to 7 hour proof)

| Mother sponge    | 17.5 lb. | (12 lb. Higluten flour; 5.5 lb. water) |
|---|---|---|
| Flour (regular)  | 100.0 lb. | |
| Water            | 57.5 lb. | |
| Salt             | 2.0 lb. | |
|                  | 177.0 lb. | bread dough (= approximately 140 1-lb. loaves) |

Pertinent information:
1. Mother sponge contributes both *L. sanfrancisco* and *T. holmii*
2. Approximately 11% of total flour is from mother sponge
3. Proof time (time after molding) = 6 to 7 hours at 82–84° F.
4. Initial pH = 5.3 to 5.4; Final pH = 3.9 to 4.0
5. Miscellaneous: no Bakers yeast added
   no sugar added
   no need for artificial acidification

EXAMPLE 31

MODIFIED "CONVENTIONAL" (6 to 7 hour proof) SOUR DOUGH BREAD FORMULATIONS FOR USE WITH SPONGES PREPARED FROM FREEZE-DRIED STARTER and PREPARATION OF THESE SPONGES

| 31-A: | Sponge having flour:water ratio = 1:0.45 (same as mother sponge): | |
|---|---|---|
| Freeze-dried starter | .06 lb. | (stabilizer-free basis) |
| Flour (Higluten)     | 12.1 lb. | |
| Water                | 5.4 lb. | (4.75lb. water; 0.65lb. 2% lactic:acetic 7:3) |

-continued
MODIFIED "CONVENTIONAL" (6 to 7 hour proof) SOUR DOUGH BREAD FORMULATIONS FOR USE WITH SPONGES PREPARED FROM FREEZE-DRIED STARTER and PREPARATION OF THESE SPONGES 17.56 lb. sponge Pertinent information on above sponge:
1. Initial: pH = 5.4; viable count of *L. sanfrancisco* = $7 \times 10^6$/g.
2. Incubate: 10 to 12 hours at 82-84° F.
3. Final: pH = 3.9; viable count of *L. sanfrancisco* = $2 \times 10^9$/g.
4. Prepared in conventional horizontal mixer

Bread dough preparation from above sponge:

| | | |
|---|---|---|
| Sponge | 17.5 lb. | (12 lb. Higluten flour; 5.5 lb. Water) |
| Flour (regular) | 100.0 lb. | |
| Water | 57.5 lb. | |
| Salt | 2.0 lb. | |
| Bakers yeast (compressed) | .05 to .07 lb. | |
| | 177.05 lb. bread dough (= approx. 140 1-lb. loaves) | |

Pertinent information on above bread dough:
1. Sponge contributes only *L. sanfrancisco*
2. Approximately 11% of total flour is from sponge
3. Proof time (time after molding) = 6 to 7 hours at 82-84° F.
4. Initial pH = 5.3 to 5.4; Final pH = 3.9 to 4.0
5. Very limited amount Bakers yeast added
6. Miscellaneous: no sugar added
   no need for artificial acidification
   no need for dough strengtheners (bromate, ascorbate)

31-B: Sponge (liquid) having flour:water ratio = 1:1

| | | |
|---|---|---|
| Freeze-dried starter | .05 lb. (stab.-free basis) | |
| Flour (Higluten) | 6.1 lb. | |
| Water | 6.1 lb. | (5.76 lb. water; 0.34 lb. 2% lactic:acetic 7:3) |
| Salt | .05 lb. | |
| | 12.3 lb. liquid sponge | |

Pertinent information on above liquid sponge:
1. Initial: pH = 5.4; viable count of *L. sanfrancisco* = $8 \times 10^6$/g.
2. Incubate: 8 to 10 hours at 82-84° F.
3. Final: pH = 3.80 to 3.85; viable count *L. sanfrancisco* = $3 \times 10^9$/g.
4. Prepared in vertical-type mixer

Bread dough preparation from above liquid sponge:

| | | |
|---|---|---|
| Liquid sponge | 12.3 lb. | (6.1 lb. Higluten flour; 6.1 lb. Water) |
| Flour (regular) | 105.9 lb. | |
| Water | 56.8 lb. | |
| Salt | 1.95 lb. | |
| Bakers yeast (compressed) | .05 to .07 lb. | |
| | 177 lb. bread dough (= approximately 140 1-lb. loaves) | |

Pertinent information on above bread dough:
1. Sponge contributes only *L. sanfrancisco*
2. Approximately 5.5% of total flour is from sponge
3. Proof time (time after molding) = 6 to 7 hours at 82-84° F.
4. Initial pH = 5.3 to 5.4; Final pH = 3.9 to 4.0
5. Very limited amount Bakers yeast added
6. Miscellaneous: no sugar added
   no need for artificial acidification
7. Low level (about 25 ppm $KBrO_3$ or 50 ppm Ascorbate) of dough strengtheners may be optionally added

31-C: Sponge (liquid) having flour:water ratio = 1:2.5

| | | |
|---|---|---|
| Freeze-dried starter | .07 lb. (stab.-free basis) | |
| Flour (Higluten) | 6.1 lb. | |
| Water | 15.3 lb. | (14.9 lb. water; 0.4 lb. 2% lactic:acetic 7:3) |
| Salt | .13 lb. | |
| | 21.6 lb. liquid sponge | |

Pertinent information on above liquid sponge:
1. Initial: pH = 5.4; viable count of *L. sanfrancisco* = $7 \times 10^6$/g.
2. Incubate: 8 to 10 hours at 82-84° F.
3. Final: pH = 3.75 to 3.80; viable count *L. sanfrancisco* = $1.5 \times 10^9$
4. Prepared in liquid sponge or slurry mixer.

Bread dough preparation from above liquid sponge:

| | | |
|---|---|---|
| Liquid sponge | 21.6 lb. | (6.1 lb. Higluten flour; 15.3 lb. water) |
| Flour (regular) | 105.9 lb. | |
| Water | 47.6 lb. | |
| Salt | 1.87 lb. | |
| Bakers yeast (compressed) | .05 to .07 lb. | |
| | 177 lb. bread dough (= approximately 140 1-lb. loaves) | |

Pertinent information on above bread dough:
1. Sponge contributes only *L. sanfrancisco*
2. Approximately 5.5% of total flour is from sponge
3. Proof time (time after molding) = 6 to 7 hours at 82-84° F.

MODIFIED "CONVENTIONAL" (6 to 7 hour proof) SOUR DOUGH BREAD FORMULATIONS FOR USE WITH SPONGES PREPARED FROM FREEZE-DRIED STARTER and PREPARATION OF THESE SPONGES
-continued 4. Initial pH = 5.3 to 5.4; Final pH = 3.9 to 4.0
5. Miscellaneous: no sugar added
   no need for artificial acidification
6. Very limited amount Bakers yeast added
7. Low level (about 25 ppm $KBrO_3$ or 50 ppm Ascorbate) dough strengtheners may be optionally added 31-D: Yields (bread) from 1 lb. of freeze-dried product with 6 to 7 hour proof In the above procedures, 31-A to 31-C, approximately 0.06 lb. (1 oz.) of the freeze-dried product of this invention are used to prepare about 140 1-lb. loaves of bread or a yield of about 2300 1-lb. loaves per 1 lb. of freeze-dried starter.

The above yield is that estimated with the starter sponge prepared in a single step. However, alternately, the starter sponges may be prepared in two steps, with the first step being identical in proportions to the formulations shown. The second step or build would be formulated with about 10% (5.5 to 12) of the flour being derived from the fully developed product of the first step. This 10% would simultaneously provide optimal levels of acidity and viable count to complete the second step in 5 to 6 hours at 82 to 84° F. In this manner a yield of approximately 20,000 lb. loaves per 1 lb. of freeze-dried starter would be obtained.

Note: In all of the sponge preparations shown in Example 31, artificial acidification was used at least in the first step. To rely entirely on the freeze-dried starter to contribute the needed acidification with lactic and acetic acids, an amount contributing a minimum of 5 to 6% of the flour in the sponge formulation would be used. Thus in Example 31-B the level of freeze-dried starter used would be increased from 0.05 lb. to 0.4 lb. This would decrease the yields obtained to about 300 lb. loaves per lb. of freeze-dried starter for a 1-step preparation or to about 2500 1-lb. loaves per lb. of freeze-dried starter for a 2-step preparation.

EXAMPLE 32

DEVELOPMENT OF SOUR DOUGH BREAD FORMULATIONS AND SPONGES FOR RAPID (approximately 1½ hr. proof) PROCESSES 32-A: Basic bread dough formulation:

| | |
|---|---|
| Special sponge | 53.5 lb. (37.2 lb. Higluten flour; 16.3 lb. water) |
| Flour (regular) | 72.3 lb. |
| Water | 46.7 lb. |
| Salt | 2.0 lb. |
| Bakers yeast (compressed) | 0.6 to 1.2 lb. |
| Sugar | 1.1 lb. |
| | 177 lb. bread dough (= approx. 140 1-lb. loaves) |

Pertinent information on above bread dough formulation developed for approximately 1½ hour proof. Those factors markedly different than those in the 6 to 7 hour proof formulations are marked with an *.

1. Sponge contributes only *L. sanfrancisco*
*2. Approximately 30-34% of total flour is from special sponge
*3. Proof time (time after molding) = 1½ hr. at 84-86° F.
*4. Initial pH = 4.4 to 4.5; Final pH = 3.95 to 4.05
*5. Substantial levels (approx. 1% based on flour) of Bakers yeast used. For shorter proof times of about 1 hour, use 2.5 to 3.0% Bakers yeast with final pH then = 4.1 to 4.2.
*6. Sugar (sucrose or dextrose) added and of vital importance
7. Addition of $KBrO_3$ (about 25 ppm) or Ascorbic Acid (about 50 ppm) desirable if special sponges are of liquid type.

32-B1: 2-step preparation of special sponges for use with 32-A bread dough formulation:

| | Step 1 | | |
|---|---|---|---|
| | Flour:water = 1:2.5 | flour-water = 1:1 | flour:water = 1:0.45 |
| Freeze-dried starter: | .05 lb. | .04 lb. | .03 lb. |
| Flour (Higluten): | 4.50 lb. | 4.61 lb. | 4.53 lb. |
| Water: | 11.25 lb. (10.96 water 0.29 2% acid) | 4.61 lb. (4.36 water 0.26 2% acid) | 2.06 lb. (1.82 water 0.24 2% acid) |
| Salt: | 0.10 lb. | 0.04 lb. | — |
| | 15.9 lb. | 9.3 lb. | 6.62 lb. |
| Time at 82–84° F.: | 8 to 10 hr. | 8 to 10 hr. | 10 to 12 hr. |
| Step 2 (all flour:water = 1:0.45) (i.e. = mother sponge type) | | | |
| Step 1 sponge: | 15.9 lb. (4.50 flour 11.25 water) | 9.3 lb. (4.61 flour 4.61 water) | 6.6 lb. (4.53 flour 2.06 water) |
| Flour (Higluten): | 32.7 lb. | 32.8 lb. | 32.6 lb. |
| Water: | 5.0 lb. | 11.4 lb. | 14.4 lb. |
| | 53.6 lb. | 53.5 lb. | 53.6 lb. |

Time at 82–84° F.: Approx. 5 to 6 hours (flour transfer from Step 1 = approx. 12% in all cases)

Note: Pertinent information on pH changes and viable count changes same as Example 31.

| 32-B2: | Alternate 2-step preparation of special liquid sponges and modified bread dough formulation for rapid (approximately 1½ hr. proof) process | | | | |
|---|---|---|---|---|---|

Step 1

15.9 lb. of flour:water = 2.5  
as in Step 32-B1 Step 1

9.3 lb. of flour:water = 1:1  
as in 32-B1 Step 1

Step 2 (all flour:water = 1:1)

| Step 1 sponge | 15.9 lb. | 4.50 flour 11.25 water) | Step 1 sponge | 9.3 lb. | 4.61 flour 4.61 water) |
|---|---|---|---|---|---|
| Flour (Higluten) | 32.7 lb. | | Flour (Higluten) | 32.7 lb. | |
| Water | 26.1 lb. | | Water | 32.7 lb. | |
| Salt | 0.32 lb. | | Salt | 0.26 lb. | |
| | 75 lb. Liquid sponge (Incubate 5 to 6 hr. at 82–84° F.) | | | 75 lb. liquid sponge | |

Step 3
Special bread dough formulation for Step 2 sponges

| Liquid sponge | 75 lb. | 37.3 flour; 37.3 water) |
|---|---|---|
| Flour (regular) | 72.3 lb. | |
| Water | 26.1 lb. | |
| Salt | 1.6 to 1.7 lb. | (total = 2.0 lb.) |
| Bakers yeast (compressed) | 0.6 to 1.2 lb. | |
| Sugar | 1.1 lb. | |
| | 177 lb. bread dough (= 140 1-lb. loaves) | |

Pertinent information on above bread dough formulation identical with that shown for Basic Bread Dough Formulation 32-A.

32-C: Yields (bread) from 1 lb. of freeze-dried product with ½ hour proof

In all of the above processes (32-B1, 32-B2), two steps were used in the preparation of the sponges. Approximately 0.04 lb. of freeze-dried starter was used to yield 140 1-lb. loaves or a yield of about 3500 1-lb. loaves per 1 lb. of freeze-dried starter.

A single step process for the preparation of the sponge for use in this rapid proof method is described below (32-D).

Note: Again, in the first step of sponge preparation, addition of artificial acidity can be made unnecessary by increasing the level of freeze-dried starter used about 7-fold in this case (cf. 32-B1) to about 0.25 lb. thereby decreasing the yield per 1 lb. of starter to about 500 1-lb. loaves.

| 32-D1: | One step preparation of special sponges for rapid (1½ hour) proof method: | |
|---|---|---|
| | Flour:water = 1:2.5 | Flour:water = 1:0.45 |
| Freeze-dried starter: | 0.25 lb. | 0.18 lb. |
| Flour (Higluten) | 37.3 lb. | 37.1 lb. |
| Water: | 37.3 lb. (35.2 water 2.1 2% acid) | 16.5 lb. (14.5 water 2.0 2% — acid) |
| Salt: | 0.32 lb. | |
| | 75 lb. liquid sponge | 53.8 lb. sponge |
| Time at 82–84° F.: | 8 to 10 hr | 10 to 12 hr |
| Preparation of Bread Dough: | of. 32-B2 Step 3 = 140 1-lb. loaves | cf. 32-A = 140 1-lb. loaves |

32-D2: Yields from one step sponge preparation in 32-D1:

| Flour:water = 1:2.5 140 loaves/0.25 lb. = | 560 1-lb. loaves per 1 lb. freeze-dried starter |
|---|---|
| flour:water = 1:0.45 140 loaves/0.18 lb. = | 778 1-lb. loaves per 1 lb. freeze-dried starter |

Note:
To eliminate need for artificial acidification in above 1-step sponge preparation, the level of freeze-dried starter used would be increased to about 2 lb. thereby decreasing yield to about 70 1-lb. loaves per lb. of freeze-dried starter.

I claim:

1. A freeze-dried bakery composition comprising Lactobacillus sanfrancisco in a flour culture media which has been subjected to incubation conditions suitable for the growth of said bacteria prior to freeze-drying, said Lactobacillus sanfrancisco being initially present in said culture media to provide an initial count of at least about $5 \times 10^6$ viable cells per gram of culture media prior to being subjected to said incubation conditions, at least about 20% of the viable bacteria produced during incubation being recoverable after freeze drying, the weight ratio of flour to water in said culture media prior to freeze-drying being about 1:1 to 1:2.5, the gluten of said flour being substantially undeveloped during said incubation, said culture media containing at least about 6% by weight of at least one disaccharide stabilizer prior to freeze-drying to improve recovery of viable Lactobacillus sanfrancisco, and a residue of water of not over about 4% by weight.

2. A freeze-dried bakery composition in accordance with claim 1 wherein said flour is high gluten flour.

3. A freeze-dried bakery composition in accordance with claim 2 wherein the weight ratio of flour to water in said culture media prior to freeze-drying is about 1:1.5 to 1:2.5.

4. A freeze-dried bakery composition in accordance with claim 2 wherein said culture media contains sodium chloride in an amount of about 0.8 to 3.0 weight percent of the water in said culture prior to freeze-drying.

5. A freeze-dried bakery composition in accordance with claim 1 wherein said composition contains at least one carbohydrate stabilizer having a substantial amount of maltose or lactose content.

6. A freeze-dried bakery composition in accordance with claim 5 in which said stabilizer is sweet whey solids.

7. A freeze-dried bakery composition in accordance with claim 5 wherein said stabilizer is present in an amount of about 6-8% by weight of the culture media prior to freeze-drying.

8. A freeze-dried bakery composition in accordance with claim 1 wherein said Lactobacillus sanfrancisco is provided in the culture by the presence of natural sponge therein.

9. A freeze-dried bakery composition in accordance with claim 8 wherein the sponge is present in an amount sufficient to produce an initial bacterial count of about $5 \times 10^8$ per ml of water in the culture media prior to freeze-drying.

10. A freeze-dried bakery composition in accordance with claim 1 wherein said culture media initially contains sufficient lactic acid and acetic acid to provide a pH of about 5.3 to 5.6.

11. A freeze-dried bakery composition in accordance with claim 10 wherein a majority of said lactic and acetic acids is present after freeze-drying.

12. A freeze-dried bakery composition in accordance with claim 1 wherein said initial count of Lactobacillus sanfrancisco is at least about $5 \times 10^7$ to $2 \times 10^8$.

13. A freeze-dried bakery composition in accordance with claim 1 wherein said stabilizer comprises at least one member selected from maltose, lactose and sucrose.

14. A freeze-dried bakery composition in accordance with claim 1 wherein said stabilizer is present in an amount of about 7.5% by weight of the final flour culture prior to freeze-drying.

15. A freeze-dried bakery composition in accordance with claim 1 wherein said incubation is executed to produce at least about $1 \times 10^9$ viable cells per gram of culture media.

16. A freeze-dried bakery composition in accordance with claim 1 wherein said residue of water is about 2% by weight.

* * * * *